US005788717A

United States Patent [19]
Mann et al.

[11] Patent Number: 5,788,717
[45] Date of Patent: Aug. 4, 1998

[54] ATRIAL RATE DETERMINATION AND ATRIAL TACHYCARDIA DETECTION IN A DUAL-CHAMBER IMPLANTABLE PACEMAKER

[75] Inventors: Brian M. Mann, Beverly Hills; Joseph J. Florio, Sunland; Laurence S. Sloman, Los Angeles, all of Calif.

[73] Assignee: Pacesetter, Inc., Sylmar, Calif.

[21] Appl. No.: 500,730

[22] Filed: Jul. 11, 1995

[51] Int. Cl.$^6$ ............................ A61N 1/36; A61B 5/0464
[52] U.S. Cl. ............................................ 607/14; 128/705
[58] Field of Search ............................ 607/9, 14, 17; 128/705, 706, 702

[56] References Cited

U.S. PATENT DOCUMENTS

| | | | |
|---|---|---|---|
| 4,429,697 | 2/1984 | Nappholz et al. | 607/9 |
| 4,485,818 | 12/1984 | Leckrone et al. | |
| 4,552,154 | 11/1985 | Hartlaub | 128/702 |
| 4,625,730 | 12/1986 | Fountain et al. | |
| 4,712,555 | 12/1987 | Thornander et al. | |
| 4,809,697 | 3/1989 | Causey, III et al. | |
| 4,815,469 | 3/1989 | Cohen et al. | 128/634 |
| 4,847,617 | 7/1989 | Silvian | 340/870.16 |
| 4,856,523 | 8/1989 | Sholder et al. | |
| 4,944,298 | 7/1990 | Sholder | |
| 4,967,746 | 11/1990 | Vandegriff | 607/9 |
| 5,085,215 | 2/1992 | Nappholz et al. | |
| 5,103,822 | 4/1992 | Duncan | |
| 5,144,949 | 9/1992 | Olson | |
| 5,269,299 | 12/1993 | Duncan | 607/9 |

*Primary Examiner*—William G. Kamm
*Assistant Examiner*—Jeffrey R. Jastrzab

[57] ABSTRACT

An implantable pacemaker accurately senses the regular atrial rhythm even though some portions of the atrial rhythm, e.g., every other P-wave, may potentially be masked or hidden within the ventricular absolute refractory period. Such sensing includes unmasking or uncovering any hidden P-waves, thereby allowing an accurate atrial rate to be determined. The hidden P-waves are uncovered by: changing the PV delay, not tracking a sensed P-wave, or comparing the incoming morphology of the atrial channel signal to a prior stored baseline morphology signal. The accurate atrial rate, once determined, allows the presence of an atrial tachycardia to be reliably confirmed, thereby enabling appropriate atrial anti-tachycardia pacing (ATP) procedures to be invoked, or mode switching from an atrial synchronous mode of operation, e.g., DDD, to a non-atrial synchronous mode, e.g., VVIR.

44 Claims, 15 Drawing Sheets

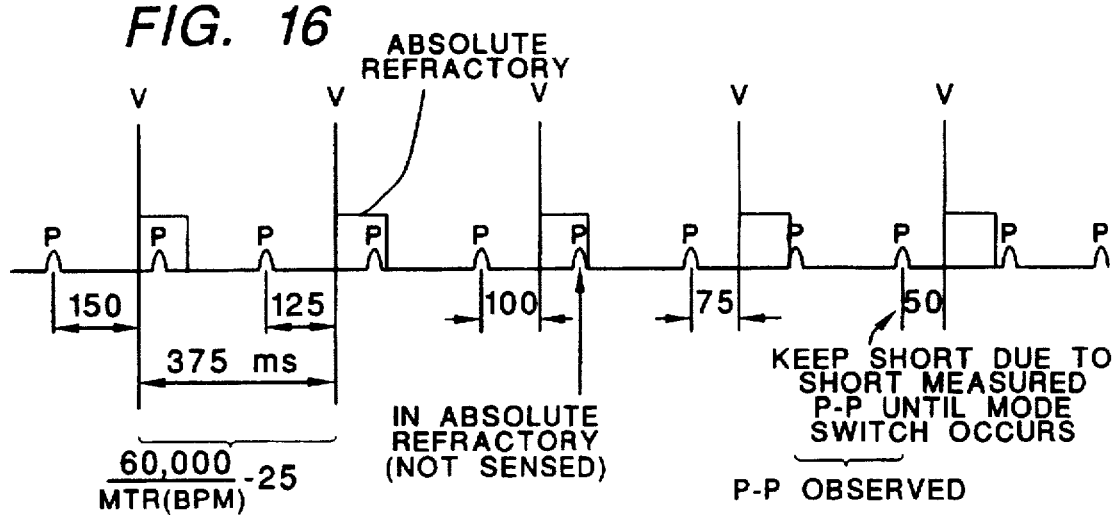
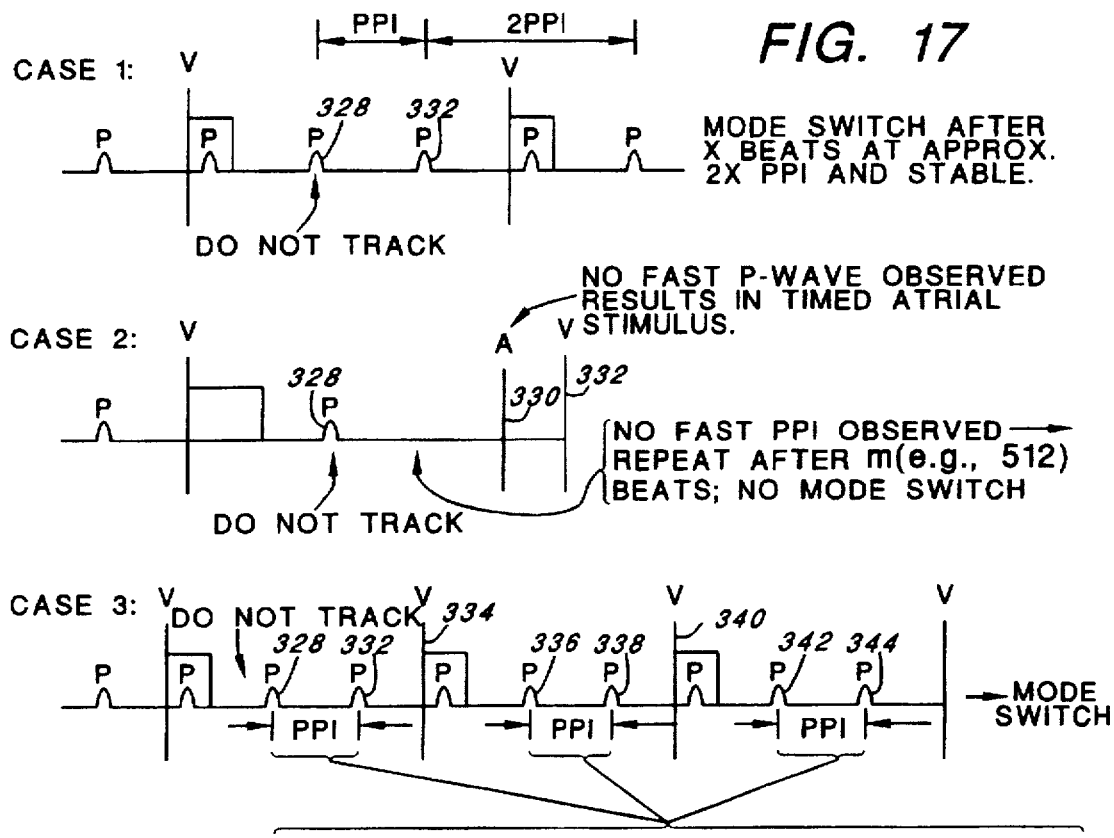

FIG. 20
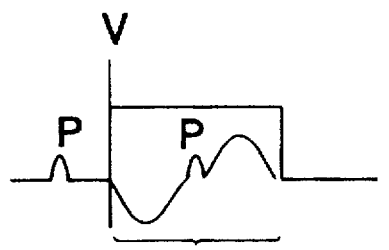
FAR FIELD R WAVE
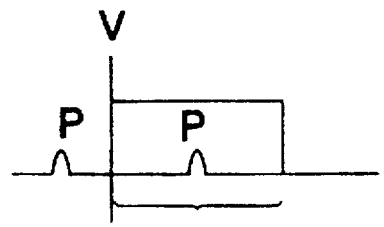
P-WAVE EXPOSED AFTER
SUBTRACTING OUT FAR
FIELD R-WAVE BASELINE
WAVE FORM

ATRIAL RATE DETERMINATION AND ATRIAL TACHYCARDIA DETECTION IN A DUAL-CHAMBER IMPLANTABLE PACEMAKER

BACKGROUND OF THE INVENTION

Field of the Invention

The present invention relates to implantable medical devices and methods, and more particularly to an improved method for detecting the atrial rate of a patient's heart using a dual-chamber implantable pacemaker. Even more particularly, the invention relates to a dual-chamber, implantable pacemaker that utilizes the determined atrial rate to detect the onset of an atrial tachycardia, and that automatically triggers a prescribed atrial tachycardia response, such as automatic mode switch (AMS) or anti-tachycardia pacing (ATP) procedures, in response to detecting the onset of such atrial tachycardia. For example, the pacemaker may utilize AMS to switch from an atrial synchronous mode to a non-atrial synchronous mode in response to detecting an atrial tachycardia.

The basic function of the heart is to pump (circulate) blood throughout the body. The blood serves as a medium for delivering oxygen and nutrients to the various tissues while removing waste products and carbon dioxide. The heart is divided into four chambers comprised of two atria and two ventricles. The atria are the collecting chambers holding the blood which returns to the heart until the ventricles are ready to receive this blood. The ventricles are the primary pumping chambers. The pumping function of the heart is achieved by a coordinated contraction of the muscular walls of the atria and the ventricles.

The atria are more than simple collecting chambers. The atria contain the heart's own (natural, native or intrinsic) pacemaker that controls the rate at which the heartbeats or contracts. In addition, the atrial contraction helps to fill the ventricle, further contributing to optimal filling and thus maximizing the amount of blood which the heart is able to pump with each contraction. Thus, atrial contraction is followed after a short period of time (normally 120 to 200 ms) by ventricular contraction.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This is termed AV synchrony.

A cardiac cycle comprises one sequence of systole and diastole. It can be detected by counting the patient's pulse rate. It is also reflected by the cardiac rhythm as recorded by an electrocardiogram (ECG) or electrogram (EGM). The ECG is a recording of the electrical activity of the heart as seen using surface electrodes placed on the surface of the body. The EGM is a recording of the electrical activity of the heart as seen using electrodes placed within the heart. An EGM that is monitored by or through an implantable pacemaker (described below) is referred to as an intracardiac electrogram (IEGM). The IEGM is seen through electrodes that form part of a pacing lead within the heart, and as sensed and saved using sensing and memory circuits within the pacemaker. The IEGM may be transmitted from the pacemaker to an external (non-implanted device) where it can be recorded and/or displayed. The electrical activity refers to the cardiac depolarization in either the atrium and/or ventricle. In general, on the ECG, EGM, or IEGM, the atrial depolarization is represented by a P-wave, while the ventricular depolarization is represented by a QRS complex, usually abbreviated as an "R-wave". The electrical depolarization triggers or initiates the active muscular contraction. Once the cardiac cells are depolarized, they must repolarize in order for the next depolarization and contraction to occur. Ventricular repolarization is represented by the T-wave. Atrial repolarization is rarely seen on an ECG or EGM as it occurs at virtually the same time as the R-wave, and is thus hidden by this large electrical signal.

A normal heart rate varies between 60 to 100 beats per minute (bpm) with an average of 72 bpm resulting in approximately 100,000 heartbeats per day. The heartbeat normally increases during periods of stress (physical or emotional) and slows during periods of rest (sleep).

The amount of blood that the heart pumps in one minute is called the cardiac output. It is calculated by the amount of blood ejected with each heartbeat (stroke volume) multiplied by the number of heartbeats in a minute. If the heart rate is too slow to meet the physiologic requirements of the body, the cardiac output will not be sufficient to meet the metabolic demands of the body. Too slow of a heart rate, termed a bradycardia, may thus result in one of two major symptoms: (1) if the heart effectively stops with no heartbeat, there will be no blood flow and if this is sustained for a critical period of time (10 to 30 seconds), the individual will faint; or (2) if there is a heartbeat but it is too slow, the patient will be tired and weak (termed low cardiac output).

A pacemaker is a medical device that is used to selectively stimulate the heart with electrical stimulation pulses aimed at assisting it to perform its function as a pump. Normally, the stimulation pulses are timed to keep the heart rate above a prescribed limit, i.e., to treat a bradycardia, but many pacemakers also include the ability to treat or stop a heart that is beating too fast, a condition known as a tachycardia. A pacemaker forms part of a pacing system. The pacing system is comprised of two major components. One component is a pulse generator which generates the stimulation pulse and includes the electronic circuitry and the power cell or battery. The other is the lead or leads which electrically couple the pacemaker to the heart.

The pacemaker delivers an electrical stimulus to the heart to cause the heart to contract when the patient's own intrinsic rhythm fails. To this end, pacemakers include sensing circuits that sense the IEGM and in particular that sense the P-waves and/or R-waves in the IEGM. By monitoring such P-waves and/or R-waves, the pacemaker circuits are able to determine the intrinsic rhythm of the heart, and provide stimulation pulses that force atrial and/or ventricular depolarizations at appropriate times in the cardiac cycle so as to help stabilize the electrical rhythm of the heart.

Pacemakers are described as either single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

A three letter code (sometimes expanded to a five letter code) is used to describe the basic mode in which the pacemaker is operating. These three letters refer specifically to electrical stimulation for the treatment of bradycardias. A fourth position (when used) identifies the degree of programmability and rate modulation, and a fifth position (when used) refers to electrical stimulation therapy for the primary treatment of fast heart rhythms or tachyarrhythmias or tachycardias.

The first position of the pacemaker code identifies the chamber to which the electrical stimulus is delivered. If the device is not capable of bradycardia support pacing, a "O" occupies this first position. If the unit paces in the ventricle, this is identified by a "V"; if it paces in the atrium, the first position is identified as an "A". If stimuli can be delivered to either the atrium or ventricle, the letter "D" is used to reflect dual-chamber stimulation.

The second position of the pacemaker code identifies the chamber or chambers in which sensing occurs. Sensing is the ability of the pacemaker to recognize the intrinsic electrical activity of the heart, e.g., to sense P-waves and/or R-waves. The letters used in this position are identical to those used in the first position.

The third position of the pacemaker code identifies the way the pacemaker responds to a sensed signal. An "I" means that the pacemaker will be inhibited. When it senses or sees an intrinsic electrical signal, it inhibits its own output pulse and resets one or more internal timers within the pacemaker's circuitry. The other basic response is represented by a "T", which means triggered. The triggered mode of response indicates that when the pacemaker senses an intrinsic electrical signal, it not only resets various internal timers within the pacemaker, it also initiates or releases a stimulus in response to that sensed event. A "D" in the third position refers to both modes of sensing response. Most commonly, a sensed signal arising from the atrium and sensed on the atrial channel of a dual-chamber pacemaker will inhibit the atrial output but trigger a ventricular output after a brief delay (the AV or PV delay). If a native ventricular depolarization does not occur before the PV delay timer completes, a ventricular stimulus will be released at the end of this PV delay. If a native ventricular signal is sensed within the PV delay, the ventricular output will be inhibited and other timers will be reset. If a native ventricular signal is sensed before the atrial stimulus is released, both the atrial and ventricular output pulses will be inhibited and the various timers will be reset.

A popular mode of operation for dual-chamber pacemakers is the DDD mode. DDD systems have been developed to overcome the limitations of previous pacing methods. Specifically, DDD systems provide atrial pacing during atrial bradycardia, ventricular pacing during ventricular bradycardia, and atrial and ventricular pacing during combined atrial and ventricular bradycardia. In addition, DDD systems provide an atrial synchronous mode. Such features more closely approximate the normal response to exercise, or other physiological activity demanding a faster heart rate, by permitting a rate increase to occur commensurate with the rate of the sensed P-wave. This advantageously increases cardiac output and facilitates maintenance of AV synchrony.

An atrial tachycardia is a fast or rapid atrial rhythm or rate. The atrial rhythm is determined within the pacemaker by measuring the time interval between consecutive P-waves within the IEGM. Should the pacemaker determine that the atrial rate exceeds some preestablished threshold, such as 200 bpm (beats per minute), then an atrial tachycardia is deemed to be present.

In response to sensing a tachycardia, it is known in the art to take appropriate corrective action, e.g., to initiate some type of prescribed antitachycardia pacing (ATP), or to switch the operating mode of the pacemaker (AMS, or "automatic mode switch"). See, e.g., U.S. Pat. Nos. 5,144,949; 5,103, 822; 5,085,215; 4,856,523; 4,944,298; and 4,485,818, each of which patents is incorporated herein by reference.

Unfortunately, the atrial sensing circuits of a dual-chamber implantable pacemaker are not able to detect all of the P-waves that occur when the atrial rate is within certain ranges. This inability to detect P-waves is due to the 2:1 block caused by the absolute refractory period following each V-pulse. That is, following every V-pulse delivered by the pacemaker, there is an absolute refractory period, or blanking period, during which the sensing circuits of the pacemaker are disabled or turned off. Within a certain range of cardiac rates, it is therefore possible for every other P-wave to fall within the absolute refractory period. Such P-waves—those occurring during the absolute refractory period—are thus "hidden" from the sensing circuits of the pacemaker and, insofar as the pacemaker is concerned, never occurred. As a result, the atrial rate determined by the pacemaker, which is based on the sensed P-waves, will not always reflect the true atrial rate, and an atrial tachycardia, even though present, may go unsensed (a false negative).

There are two types of 2:1 blocking that should be distinguished for purposes of this patent application: 2:1 sensing block, and 2:1 tracking block. Generally, 2:1 blocking refers to every other P-wave falling into a post ventricular atrial refractory period (PVARP) and not being tracked. To facilitate mode switching, some pacemakers detect but do not track P-waves which fall after the absolute refractory period but still during PVARP. As used within this patent application, "2:1 sensing block" refers to P-waves that are not detected (i.e., not sensed) as well as not tracked; whereas "2:1 tracking block" refers to P-waves that are detected (sensed), but are not tracked.

From the above, it is evident that what is needed is an improved method for determining if an atrial tachycardia is present. More particularly, what is needed is a method or technique for reliably detecting the presence of hidden P-waves so that an accurate atrial rate can be determined. Such determination, in turn, would permit a reliable detection of an atrial tachycardia, as well as a timely, appropriate response to such detection, e.g., by the pacemaker AMS and/or ATP circuits.

SUMMARY OF THE INVENTION

The present invention addresses the above and other needs by providing an implantable pacemaker capable of accurately sensing the regular atrial rhythm, despite the fact that some portions of the atrial rhythm, e.g., every other P-wave, could potentially be masked or hidden within the absolute refractory period following the ventricular stimulus. The present invention thus provides a method for unmasking hidden P-waves that potentially occur during the absolute refractory period following a ventricular stimulus (V-pulse).

Hidden P-waves are particularly likely to occur on a recurring basis when the atrial rate falls within certain ranges that make it possible for every other P-wave to be blocked or masked by the absolute refractory period (a condition known as 2:1 sensing block). The unmasking of the hidden P-waves in accordance with the present invention thus provides a means for the pacemaker circuits to reliably detect an accurate atrial rate. The accurate atrial rate, in turn, allows the presence of an atrial tachycardia to be reliably confirmed, thereby enabling appropriate atrial automatic mode switching (AMS) or atrial anti-tachycardia pacing (ATP) procedures to be invoked, such as mode switching from an atrial synchronous mode of operation, e.g., DDD, to a non-atrial synchronous mode, e.g., VVIR.

In accordance with one aspect of the invention, the method of detecting hidden P-waves involves periodically, e.g., every n cardiac cycles, changing the PV delay. The changed PV delay, in turn, causes the V-pulse to be delivered at a different time within the cardiac cycle, thereby "time-shifting" the absolute refractory period that follows the V-pulse (which absolute refractory period acts as a "blind spot" that hides any P-waves or other cardiac activity occurring during such period) to a different location within the cardiac cycle. Such time-shifting of the absolute refractory period thus uncovers any P-waves that may have been previously hidden by the absolute refractory period. Should a hidden P-wave be uncovered, then the PV delay is kept at its changed value until the presence of subsequent P-waves (which also would have been hidden) can be confirmed, from which subsequent P-waves an accurate atrial rate is determined. Once an accurate atrial rate is determined, appropriate therapy, such as mode switching, is invoked. Should a hidden P-wave not be discovered, then the normal PV delay is reinstated, but with periodic changing of the PV delay, e.g., every m cardiac cycles, to sample for the presence of any potentially hidden P-waves. The PV delay may be either shortened or lengthened when it is changed using this method, although the preferred PV change is to shorten it.

In accordance with another aspect of the invention, when the PV delay or interval is shortened in accordance with the above unmasking method (used to uncover any potentially hidden P-waves), the PV delay is decrementally shortened, rather than shortened in one big step, in order to prevent V-to-V intervals from occurring that are too short. (A short V-to-V interval represents a rapid ventricular rate, which is generally an undesirable condition for a pacemaker patient.) Hence, in carrying out this aspect of the invention, the V-to-V interval is limited to a preselected value, e.g., the maximum tracking rate (MTR) interval less 25 milliseconds, and the PV interval is shortened in a given cardiac cycle only by an amount that maintains the V-to-V interval at a value that is always greater than or equal to the preselected V-to-V interval limit. Such decrementing continues until either: (1) a minimum PV interval is reached; or (2) a P-to-P rate is revealed that is faster than the rate of predicted hidden P-waves. The first criteria for ceasing decrementing of the PV interval is absolute, the second is dynamic, and the pacemaker may be initially configured to utilize one or the other of these criteria. As with the basic PV-delay changing method described above, once a hidden P-wave is uncovered to reveal a short P-to-P interval, then the PV interval is kept at its short value until a mode switch, or other ATP therapy, is invoked.

In accordance with a further aspect of the invention, potentially hidden P-waves may be uncovered by deliberately not tracking a P-wave on a sampled basis, e.g., by not tracking a P-wave every n cardiac cycles, where n is an integer of between, e.g., 4 and 128. When a P-wave is not tracked, a PV delay is not triggered, so no V-pulse is generated, and no absolute refractory period is present that could hide a P-wave. Thus, a non-tracked P-wave effectively "opens up" or "unmasks" the blind spot that is caused by the presence of the absolute refractory period, and thereby allows any P-wave that occurs during such unmasked time to be detected.

Should a P-wave be detected during the unmasked time period following a non-tracked P-wave (which detected P-wave may be referred to herein as a "fast P-wave" because it evidences the presence of a P-to-P interval that is faster than what would be sensed if P-waves remained hidden), then the P-to-P interval defined by the fast P-wave may be used as a more accurate indicator of the actual or true atrial rate.

In accordance with the above aspect of the invention (wherein a P-wave is not tracked on a sampled basis), the actual or true atrial rate is typically confirmed when a fast P-wave is detected in one of two ways. First, normal P-wave tracking may be reinstated after sensing the fast P-wave. Such normal P-wave tracking will mask out subsequent fast P-waves, but the time interval between the sensed P-waves will be about two times the P-to-P interval determined with the fast P-wave if a 2:1 sensing block condition is present. Hence, if the measured P-to-P interval after reinstating tracking remains stable at a rate that is about two times the sensed P-to-P interval determined from the fast P-wave, then a 2:1 block condition is confirmed and the true atrial rate may be correctly ascertained from the fast P-wave. Second, the non-tracked interval may be repeated every other cycle for a prescribed number of times, e.g., 2 to 8. If a fast P-wave is sensed in each of the non-tracked intervals, and if the P-to-P interval in each non-tracked interval remains about the same and within prescribed limits, then such P-to-P interval is used as an accurate indicator of the true atrial rate.

Further, in accordance the above aspect of the invention (wherein a P-wave is not tracked on a sampled basis), if a fast P-wave is not detected following a non-tracked P-wave, then an A-pulse is generated and delivered to the atrium after a timed delay of, e.g., 350 msec. The purpose of the timed delay is to allow sufficient time for the atrial tissue to repolarize following the occurrence of the non-tracked P-wave. After m cardiac cycles, where m is a programmable integer of between 128 and 512, this process repeats. That is, m cardiac cycles after sampling for a fast P-wave and not finding one, another P-wave is deliberately not tracked, and a new determination is made as to whether a fast P-wave follows such non-tracked P-wave.

Another way in which the present invention looks for potentially hidden P-waves, in accordance with still an additional aspect thereof, is to measure and save a baseline morphology of the atrial IEGM following the ventricular pulse and subtract such baseline morphology from the incoming atrial IEGM morphology during operation of the pacemaker at those times when 2:1 block condition might exist. In accordance with this morphology approach, a baseline shape of the atrial intracardiac electrogram (AIEGM) waveform sensed by the atrial channel of the pacemaker is digitized and saved in memory. This baseline morphology is taken during the ventricular absolute refractory period when it is known no hidden P-waves are present. During operation of the pacemaker, when the tracked rate is in the range where 2:1 block could occur, the morphology of the incoming atrial IEGM following delivery of a V-pulse is periodically sampled, and then subtracted from the previously-saved baseline morphology. Such subtraction will reveal a hidden P-wave, if present. The baseline morphology is updated periodically or by physician command.

Yet another way in which the present invention looks for potentially hidden P-waves, in accordance with still an additional aspect thereof, is utilized whenever the pacer is pacing at the maximum tracking rate. DDD pacers include a limit on the maximum rate at which every P-wave will be followed by a ventricular pulse. The standard algorithm used is a Wenkebach response which progressively delays the tracked ventricular stimulus until a P-wave falls within PVARP and is not tracked. A patent application of Bornzin et al., filed concurrently herewith by the same assignee as the present invention, entitled "Improved Upper Rate Response for Implantable Pacemaker Based on Atrial Lock Interval Pacing," incorporated herein by reference, provides for a PV Interval Lock upper rate response wherein the PV interval is preserved, but periodically does not track P-waves. The present invention utilizes such non-tracked cycles to unmask potential hidden P-waves. Should a prescribed number of consecutive non-tracked intervals result in an atrial rate determination that indicates a tachycardia is present, then an appropriate ATP or AMS is initiated. The intervening tracked P-waves are ignored for purposes of determining atrial rate.

It is thus a feature of the present invention to provide an improved method for reliably detecting the atrial rate sensed by the detection circuits of an implantable dual-chamber pacemaker.

It is another feature of the invention to provide such an improved atrial rate detection method in combination with mode switching and/or other atrial ATP procedures invoked by the implantable pacemaker when the detected atrial rate indicates the presence of an atrial tachycardia.

It is a further feature of the invention to provide a method of unmasking or uncovering potentially hidden P-waves that may occur within the absolute refractory period following a ventricular stimulus delivered by an implantable pacemaker.

It is yet an additional feature of the invention, in accordance with one embodiment thereof, to provide such a method of unmasking or uncovering hidden P-waves that gives preference to such uncovered P-waves in determining the atrial rate.

BRIEF DESCRIPTION OF THE DRAWINGS

The above and other aspects, features and advantages of the present invention will be more apparent from the following more particular description thereof, presented in conjunction with the following drawings (not drawn to scale) wherein:

FIGS. 11–20 are timing/waveform diagrams that illustrate how hidden P-waves are detected using the methods set forth in the flow charts of FIGS. 6–10.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that is able to uncover hidden P-waves so that an accurate atrial rate determination can be made. While there are many applications that require, or could benefit from, an accurate atrial rate determination, the preferred application described herein uses the accurate atrial rate determination to provide an indication of the onset of an atrial tachycardia, thereby enabling an appropriate AMS, or ATP therapy, to occur. It is to be understood, however, that the invention is not limited to just AMS and/or ATP applications, but applies broadly to any application where an accurate atrial rate is needed or desired.

In the description of the invention that follows, reference will first be made to FIG. 1, where a functional block diagram of a dual-chamber pacemaker 10 is illustrated. Such functional diagram is used to initially teach the primary functions carried out by the pacemaker 10. Various embodiments of the actual components used within the pacemaker 10 to carry out the pacemaker functions will then be described in conjunction with FIGS. 2–5. Next, techniques or methods used by the pacemaker 10 to implement the present invention will be described in conjunction with the flow diagrams of FIGS. 6–10 and the timing/waveform diagrams of FIGS. 11–20.

Advantageously, a wide variety of dual-chamber pacemaker configurations and pacemaker components and/or hardware may be used to implement the invention. The descriptions that follow are only exemplary of a few such configurations.

Figure 1:
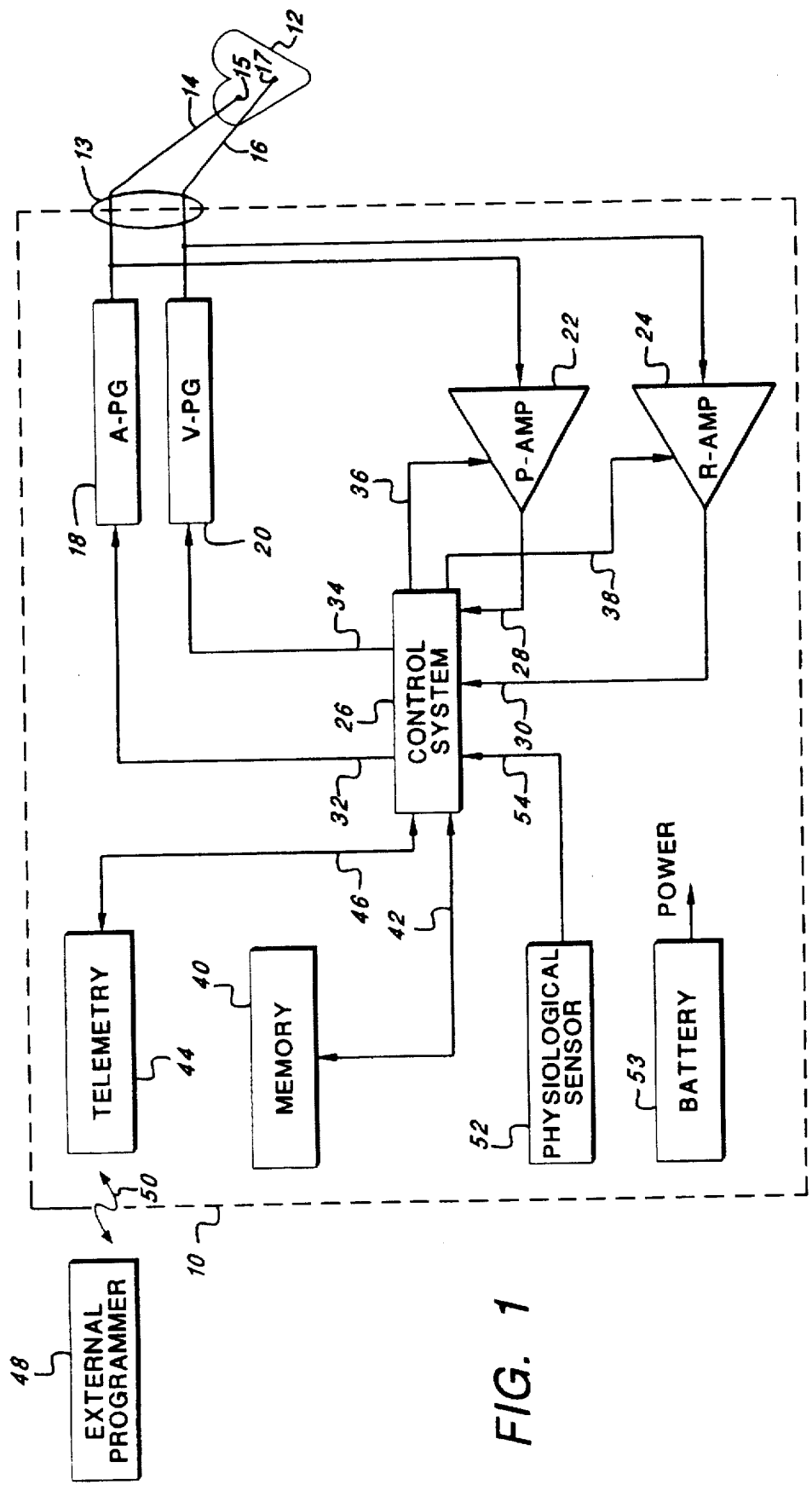
FIG. 1 is a functional block diagram of an implantable dual-chamber pacemaker.

Referring first to FIG. 1, a pacemaker 10 is coupled to a heart 12 by way of leads 14 and 16. (Note, in subsequent figures, e.g., FIG. 2, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves.

Still referring to FIG. 1, the pacemaker 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI) and the maximum tracking rate interval (MTRI). Further, data sensed during the operation of the pacer may be stored in the memory 40 for later retrieval and analysis.

A telemetry circuit 44 is further included in the pacemaker 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50. The communication link 50 may be any suitable electromagnetic link, such as an RF (radio frequency) channel, inductive coupling, or the like. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacer 10. In this manner, noninvasive communications can be established from time to time with the implanted pacer 10 from a remote, non-implanted location. Many suitable telemetry circuits known in the art that may be used with the present invention for the telemetry circuit 44. See, e.g., U.S. Pat. No. 4,847,617, incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel. Throughout the discussion that follows, reference may be made to "atrial channel activity" or "ventricular channel activity." Atrial channel activity comprises either the sensing of a P-wave by the sense amplifier 22, or the generating of an A-pulse by the A-pulse generator 18. Similarly, ventricular channel activity comprises either the sensing of an R-wave by the sense amplifier 24 or the generation of a V-pulse by the V-pulse generator 20.

In some pacemakers that implement the present invention, the pacemaker 10 may further include one or more physiological sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, and the like, may also be used in lieu of, or in addition to, an activity sensor. The type of sensor, if any, used is not critical to the present invention. Any sensor or combination of sensors capable of sensing some physiological parameter relatable to the rate at which the heart should be beating can be used. A pacemaker using such sensors is commonly referred to as a "rate-responsive" pacemaker because it adjusts the pacing rate (escape interval) of the pacer in a manner that tracks the physiological needs of the patient.

Figure 2:
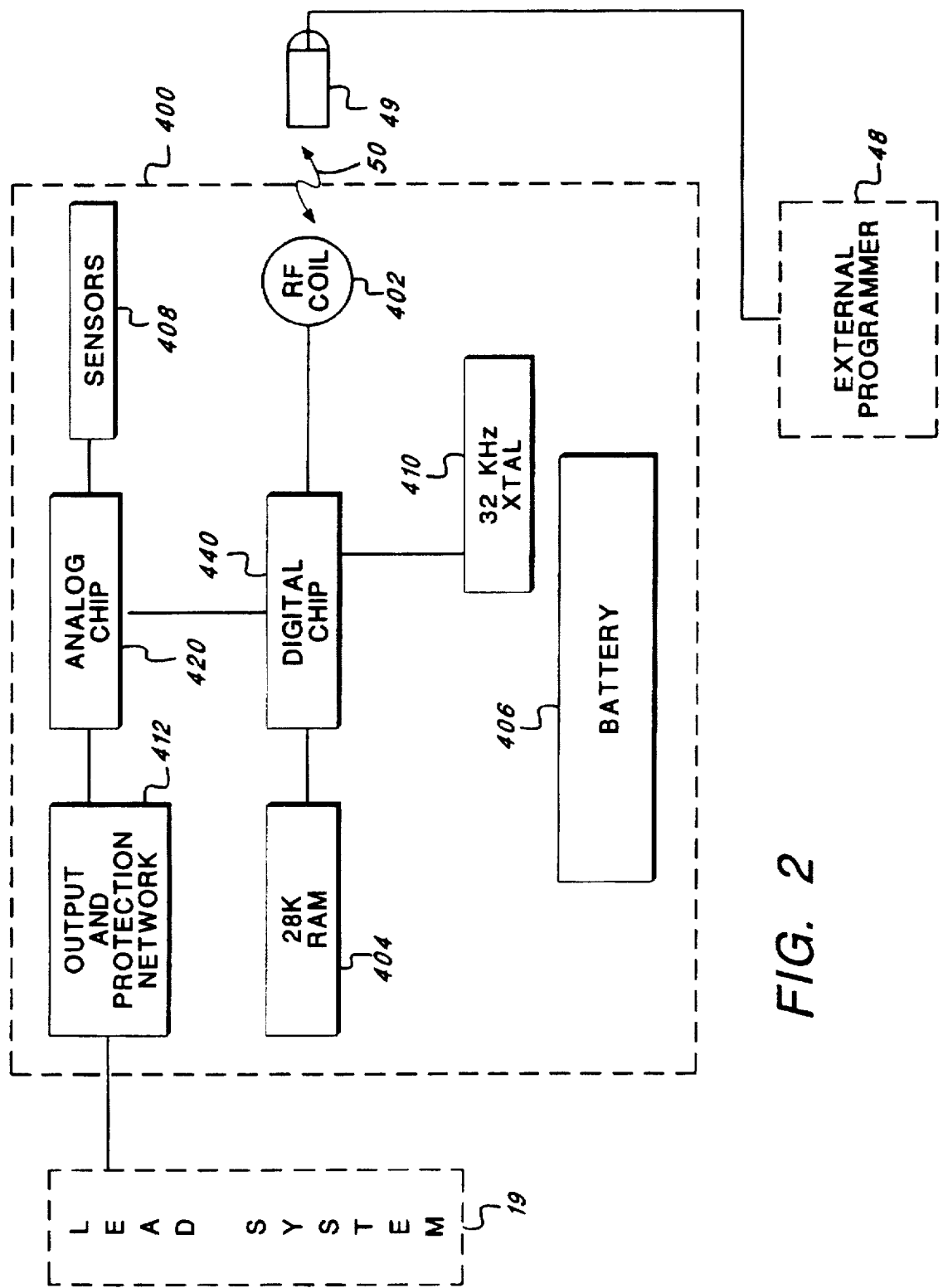
FIG. 2 is a block diagram of a pacing system that depicts, in accordance with a preferred embodiment of the invention, the main hardware components of an implantable pacemaker.

Referring next to FIG. 2, there is shown a preferred configuration for a pacing system that implements the present invention. The system includes the external programmer 48, the implantable pacemaker 10, and the lead system 19. The lead system 19 includes conventional atrial and ventricular leads and electrodes, as described previously. The lead system 19 may also include an oxygen sensor lead, which lead contains an LED-detector assembly used to measure the oxygen content of the blood. Such a lead is described, e.g., in U.S. Pat. No. 4,815,469, incorporated herein by reference.

The external programmer 48 includes a telemetry head 49 that is positioned proximate the implantable pacemaker 10 whenever the communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 2 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Figure 3:
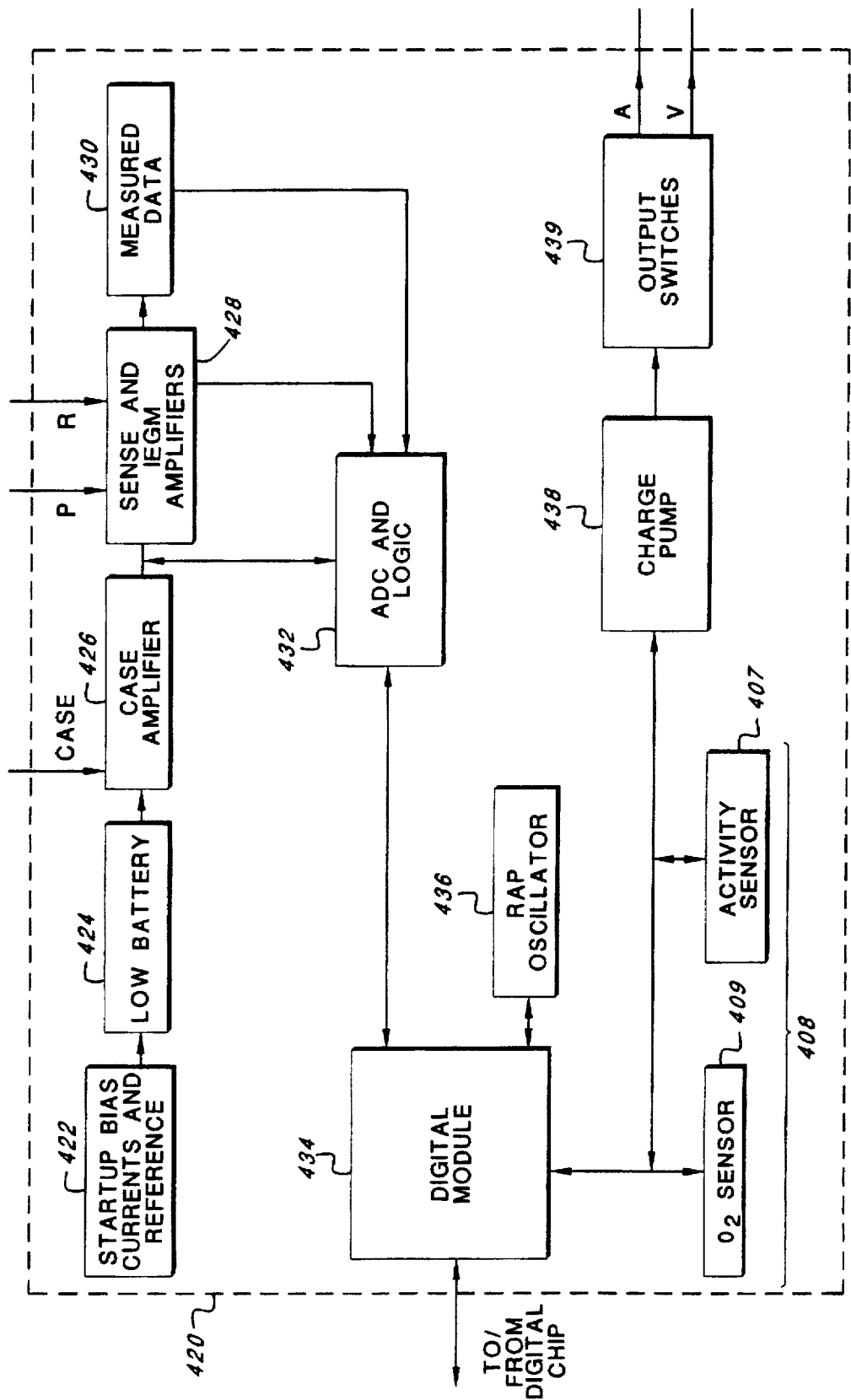
FIG. 3 is a block diagram of the analog chip portion of the pacemaker of FIG. 2.

Referring next to FIG. 3, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter and timing logic that are used to convert the analog signals of the pacemaker in to 8-bit digital words. These digital words are then passed to a digital module 434, which module is used to generate all the basic timing and bus control functions as data is passed back and forth between the analog chip 420 and the digital chip 440.

Still referring to FIG. 3, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an O2 sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 4:
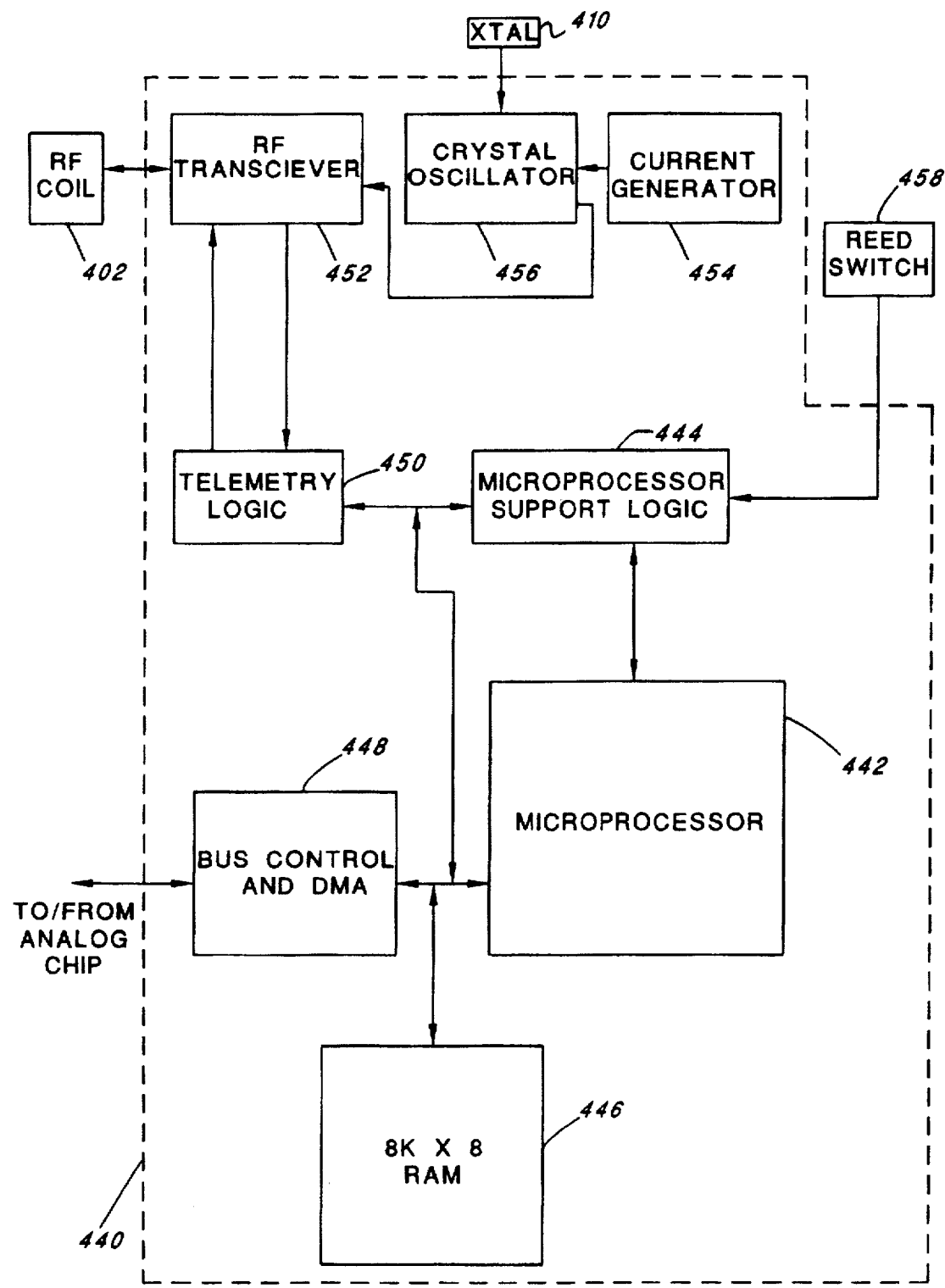
FIG. 4 is a block diagram of the digital chip portion of the pacemaker of FIG. 2, and illustrates the use of a microprocessor to control the operation of the pacemaker.

Turning next to FIG. 4, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit). In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including timing and control of the analog-to-digital converter 432 (FIG. 10) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 9). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever a test magnet is in place on the patient's skin above the location where the pacemaker is implanted.

The pacemaker circuitry described in connection with FIGS. 2–4 above provides the basic functions of the pacemaker described in connection with FIG. 1, plus other pacing/sensing functions as are known in the art. For purposes of the present invention, the pacemaker circuitry of FIGS. 2–4 sets the basic timing of the pacing interval, including setting a PV interval, a VA interval, and an MTRI. The circuitry also provides for sensing or detecting natural ventricular events (R-waves) and/or natural atrial events (P-waves), and for measuring the time interval between sensed atrial events, i.e., a P-to-P interval, and paced ventricular events, e.g., a V-to-V interval.

Figure 5:
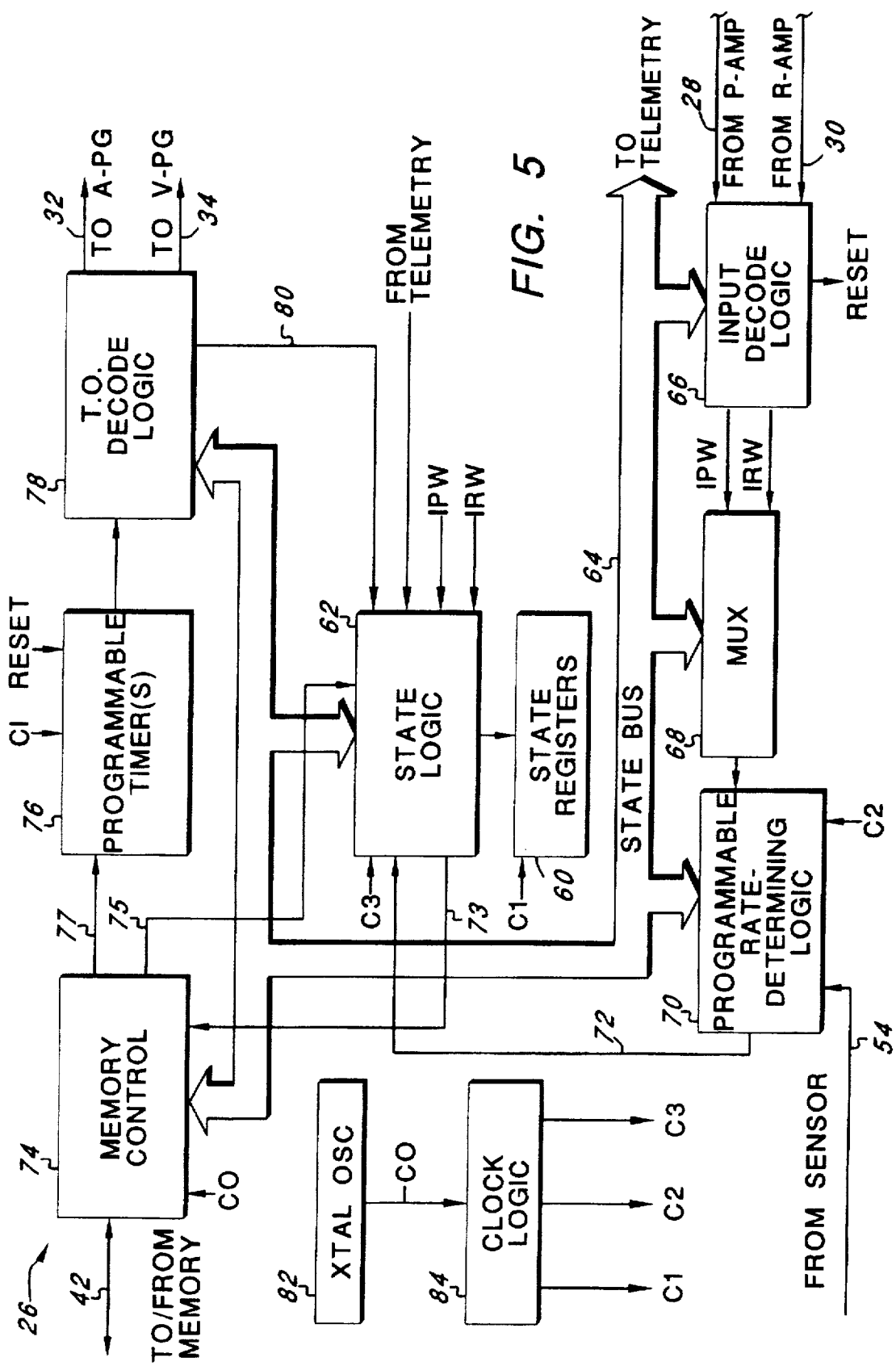
FIG. 5 is a block diagram of a state-machine based dual-chamber pacemaker of a type that could be used to implement the present invention.

Referring next to FIG. 5, a block diagram of an alternative embodiment of the control circuit or system 26 of the pacer 10 (FIG. 1) is illustrated. It is noted that in addition to the embodiment of the invention illustrated above in FIGS. 2–4, or below in FIG. 5, that still other embodiments of a control system 26 may be utilized. The embodiment described above in FIGS. 2–4 shows a control system and pacemaker configuration that is based on a microprocessor. Another representative microprocessor-based system is described, for example, in U.S. Pat. No. 4,940,052, entitled "Microprocessor Controlled Rate-Responsive Pacemaker Having Automatic Threshold Adjustment," incorporated herein by reference.

The control system shown in FIG. 5 is based on a state machine wherein a set of state registers 60 define the particular state of the pacer at any instant in time. As is known in the art, state machines may be realized using dedicated hardware logic circuits, or a suitable processor (programmed-controlled circuit) to simulate such dedicated hardware logic circuits. However implemented, the results are the same—the state of the pacer is defined at any instant of time by the pacemaker logic and sensed events which transpire or fail to transpire, such as the sensing of an R-wave, or the timing out of a timer. A complete description of FIG. 5, including basic state machine operation, may be found in the patent applications that have been incorporated herein by reference. The various circuits of the control system 26 of FIG. 5, or simulated equivalents thereof, may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their interrelationships are more thoroughly described; and U.S. Pat. No. 4,944,298 wherein an atrial-rate based programmable pacemaker is described, including a thorough description of the operation of the state logic used to control such a pacemaker. The '555, '980 and '298 patents are also incorporated herein by reference.

The details of the control system 26, whether based on a microprocessor, state machine, or other type of control devices, or simulated control devices, are not critical to an understanding or implementation of the present invention, and hence are not presented herein. Such details may be found in the referenced applications and patents, if desired. All that is significant for purposes of the present invention is that the control system of the pacemaker be capable, in conjunction with other pacemaker circuitry, of setting the pacing interval, and the various subintervals that make up the pacing interval, e.g., the PV interval, the VA interval and the MTR interval; tracking events that occur during a given defined interval; keeping track of the number of cardiac cycles that have elapsed; measuring the P-to-P interval, the V-to-V interval, and other intervals defined by sensed or paced events; storing indicated measured values for later reference or processing; and carrying out whatever processing of these measured intervals or stored values is required, e.g., averaging, comparing, and the like.

Given a pacemaker constructed as described above in connection with FIGS. 1-5, or an equivalent pacemaker, one aspect of the present invention relates to a method of controlling such a pacemaker, or a method of operating such a pacemaker, so that a more accurate atrial rate can be determined. An important application for using such a method is to allow the onset of an atrial tachycardia to be accurately determined so that appropriate automatic mode switch (AMS) and/or anti-tachycardia pacing (ATP) therapy may be invoked. While an AMS application is described below, it is to be emphasized that the present invention is not limited to just an AMS application. Rather, the invention may be utilized for any purpose where an accurate atrial rate measurement is needed.

Figure 6A:
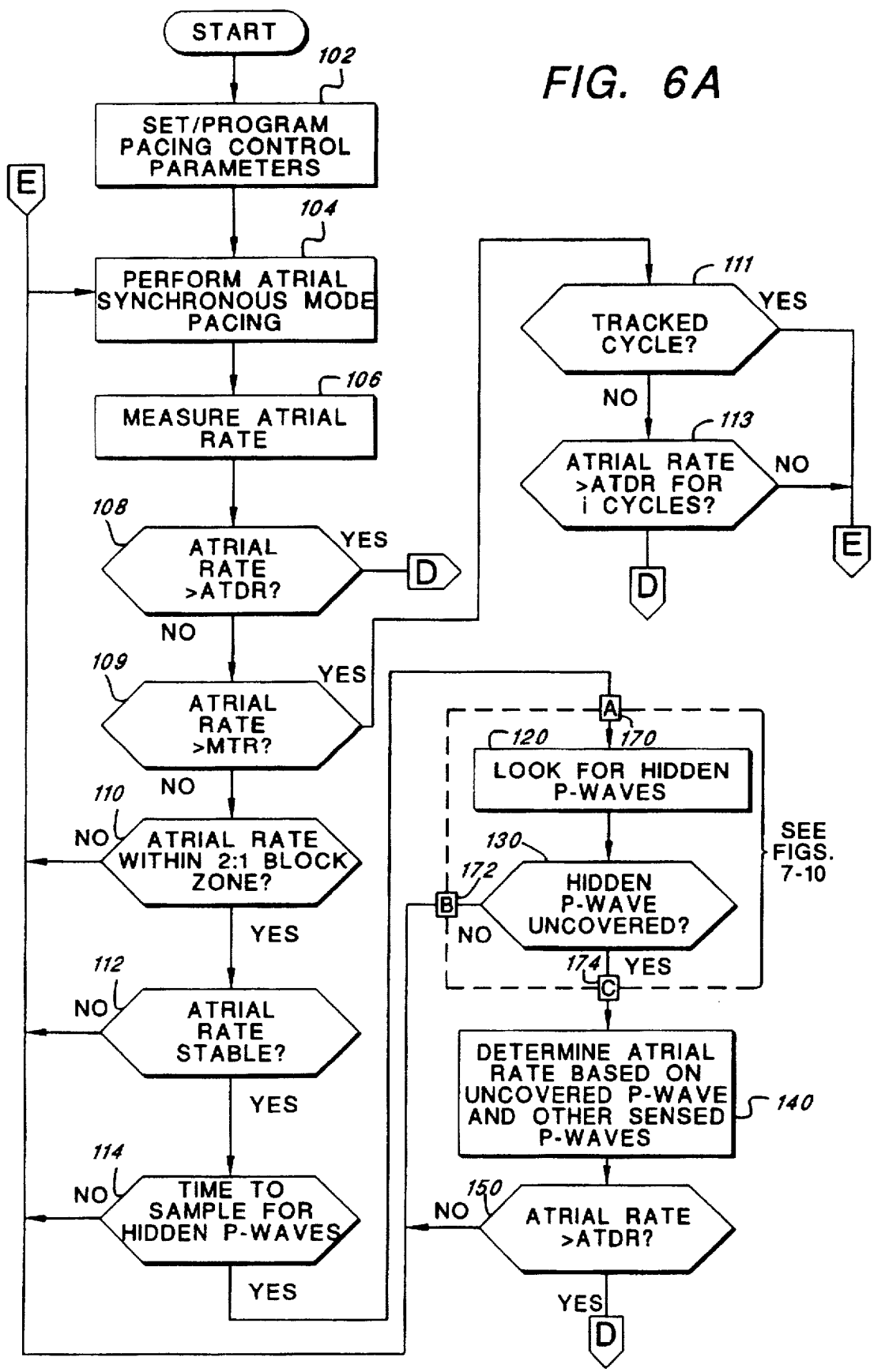
FIG. 6 is flow chart that provides an overview of the manner in which the present invention uses the determined atrial rate to apply appropriate AMS and/or ATP therapy, when needed.
Figure 6B:
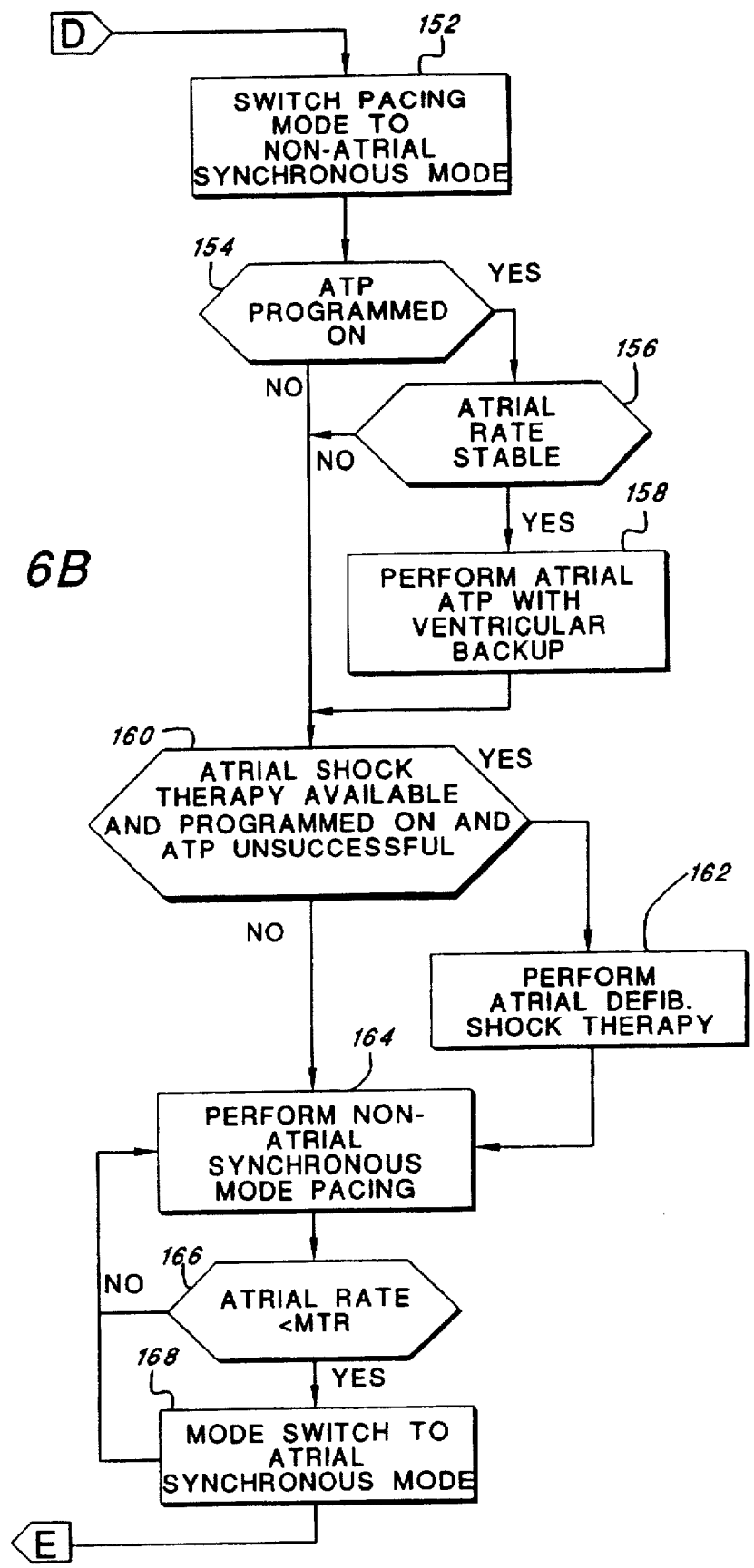

Turning then to FIGS. 6A and 6B (note: FIGS. 6A and 6B show different portions of the same overall flow diagram), the method used by the invention to accurately detect the true atrial rate of the patient so that the onset of an atrial tachycardia can be reliably determined is shown. In FIGS. 6A and 6B, and the other flow diagrams or flowcharts used herein, each main step of the process or sequence is shown as a "block" or "box", with each block having a reference numeral assigned thereto to aid in the explanation thereof. Such flowchart is particularly helpful when the invention is implemented using a microprocessor, or equivalent processing device, that follows a stored program, with the flowchart depicting an outline or structure of the stored program.

The method of the invention is intended for use with atrial synchronous pacing modes, e.g., any mode that tracks P-waves and uses such tracked P-waves as an indication of the atrial rate. An example of an atrial synchronous mode is DDD or VDD.

The method of detecting a true atrial rate depicted in FIGS. 6A and 6B first includes initially setting the programming and pacing parameters of the pacemaker (block 102). Such parameters include, e.g.: the desired atrial synchronous mode of operation for the pacemaker; the amount by which the PV delay is to be shortened or lengthened when looking for hidden P-waves; the sampling period (measured in cardiac cycles) that is to elapse before looking for hidden P-waves; the minimum value that the PV delay may assume (assuming a shortening or the PV delay is used); the minimum value for a V-to-V interval (to limit the step size of a shortening of the PV interval); and other similar parameters as detailed below.

Once the pacing parameters are set, then the atrial synchronous pacing mode is carried out (block 104). As part of carrying out the atrial synchronous mode, the atrial rate is determined (block 106). Typically, such rate is determined by measuring the P-to-P interval, or averaging the measured P-to-P interval over a prescribed number of cardiac cycles. If the measured atrial rate is greater than a preset atrial tachycardia detection rate (ATDR) (block 108), then appropriate AMS and/or ATP procedures are invoked (blocks 152-168), as explained more fully below.

When the atrial rate is less than the ATDR (NO branch of block 108), then a determination is made as to whether the atrial rate is greater than the maximum tracking rate (MTR) (block 109). If not (NO branch of block 109), then operation of the pacemaker is resumed at block 110, described below.

If the atrial rate is determined to be greater than the MTR (YES branch of block 109), then a determination is made as to whether the detected P-wave was tracked (block 111). If so, then operation is resumed at "E" (block 104). If not, then the atrial rate is remeasured (block 113). If the remeasured atrial rate is greater than the ATDR for i consecutive non-tracked cycles, e.g., 3, then a mode switch is initiated at "D" (block 152, FIG. 6B). If not, then operation of the pacemaker is resumed at "E" (block 104).

Figure 18:
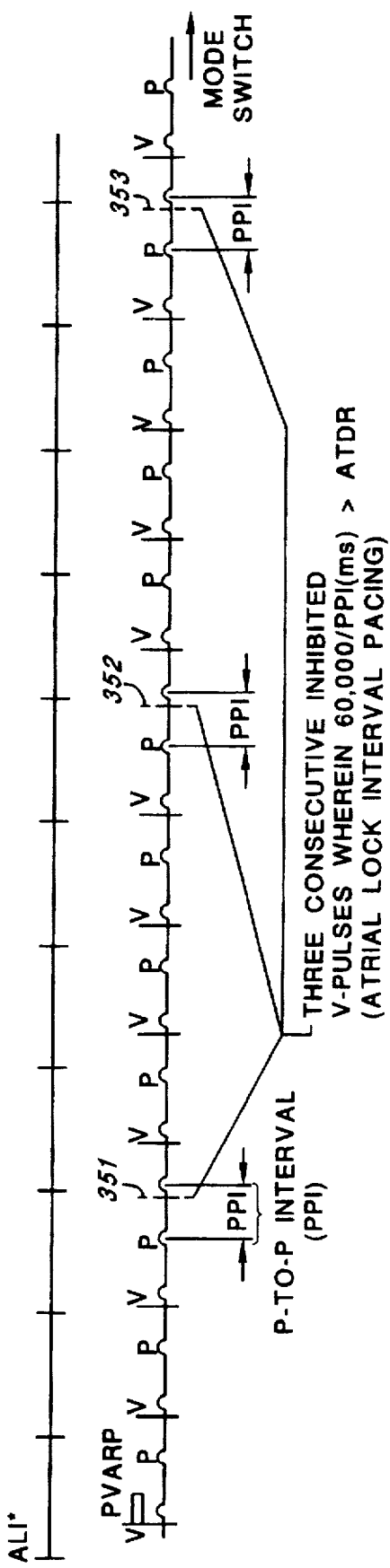
Figure 19:
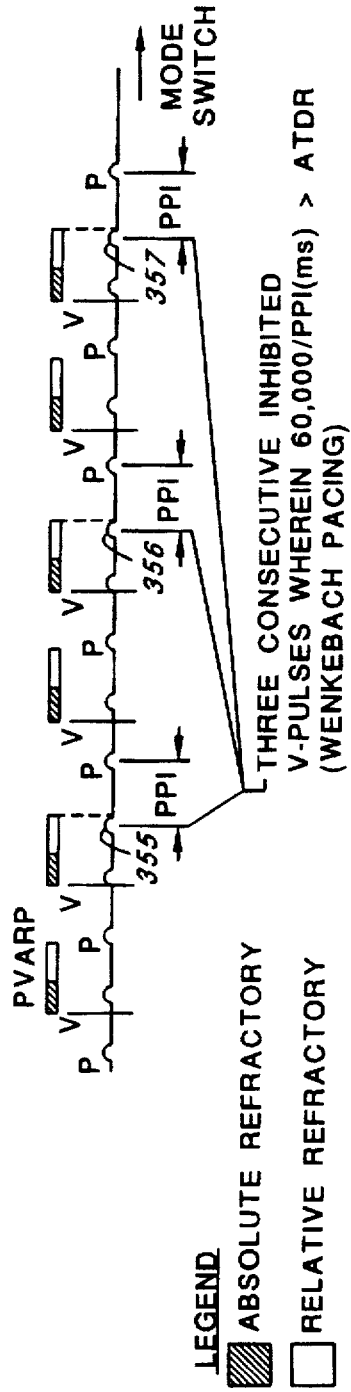

To further illustrate operation of the invention when the atrial rate is greater than MTR (YES branch of block 109), reference is momentarily made to FIGS. 18 and 19. In accordance with an upper rate response provided by the invention, if the atrial rate is greater than MTR, then the pacemaker paces at or near the maximum tracking rate (MTR). At the MTR, the usual pattern followed by the pacemaker is a Wenkebach response. During Wenkebach, the tracked ventricular stimulus is progressively delayed (i.e., the PV interval is progressively increased) until a P-wave falls within PVARP and is not tracked. Also, a recent invention provides for a PV Interval Lock upper rate response (also referred to as Atrial Lock Interval pacing) wherein the PV interval is preserved, but periodically does not track P-waves, as described in the Bornzin reference, cited previously. Hence, in either a Wenkebach response or an Atrial Lock Interval response, there are cycles or intervals during which P-waves are not tracked, even though sensed.

The present invention advantageously uses the non-tracked cycles of a Wenkebach response or an Atrial Lock Interval response to unmask potentially hidden P-waves. As seen in FIG. 18, for example, which shows Atrial Lock Interval (ALI) pacing, a ventricular stimulus "V" (V-pulse) tracks every other P-wave 350, with other P-waves being hidden (not sensed nor tracked) during the post ventricular absolute refractory period (PVARP) following each V-pulse. However, in accordance with ALI pacing, an ALI* period is defined that is free running (not synchronized with any cardiac events), and only one V-pulse is permitted during each ALI* period. In the event a second V-pulse would be generated during a given ALI* period, the second V-pulse is inhibited. Thus, as seen in FIG. 18, a V-pulse 351 would normally occur but for the fact that it represents the second V-pulse of the current ALI* period. Thus, the V-pulse 351 is inhibited, and the next P-wave is tracked, thereby uncovering the P-wave that would otherwise have remained hidden after the V-pulse 351. In a similar manner, V-pulses 352 and 353 are also inhibited in order to prevent more than one V-pulse per ALI* period, thereby unmasking additional hidden P-waves. If a prescribed number of V-pulses, e.g., three, are inhibited in this manner, and if the P-to-P interval (PPI) associated with the hidden P-wave thus uncovered evidences an atrial rate that is greater than the atrial tachycardia detection rate (ATDR), then the pacing mode is switched. For example, if the ATDR is expressed in beats per minute, and if the PPI is measured in milliseconds (msec), and if three consecutive ALI* periods occur during which a second V-pulse would occur (but for the fact that it is inhibited), and if the PPI associated with the P-waves uncovered as a result of inhibiting the second V-pulse satisfies the expression $$60,000/PPI(msec)>ATDR,$$

then that indicates a fast atrial rate (tachycardia) is present. Accordingly, an appropriate mode switch occurs in an attempt to break the atrial tachycardia as described more fully below in connection with FIG. 6B.

In FIG. 19, which shows a Wenkebach response, a hidden P-wave 355 occurs during the relative refractory portion of PVARP, and such P-wave is thus not tracked. (PVARP, or the "post ventricular atrial refractory period", is depicted in FIG. 19 as a horizontal bar that starts with the V-pulse and continues thereafter for a set time. The absolute refractory portion of PVARP, during which no sensing occurs, is shown as a cross-hatched bar, while the relative refractory portion of PVARP, during which P-waves may be sensed, but not tracked, is shown as a hollow bar.) Similarly, P-waves 356 and 357 occur during PVARP at a time when, although sensed, they are not tracked. In accordance with the present invention, when a prescribed number i of consecutive non-tracked P-waves occur, e.g., i=3 (where a non-tracked interval comprises a non-tracked P-wave followed by a tracked P-wave), and if such intervals evidence an atrial rate greater than the ATDR, then a mode switch occurs, as described below in connection with FIG. 6B. Note that intervening tracked P-waves 350 are not used for the purpose of determining the atrial rate.

Thus, it is seen that the present invention advantageously uses non-tracked intervals to measure the atrial rate.

Figure 11:
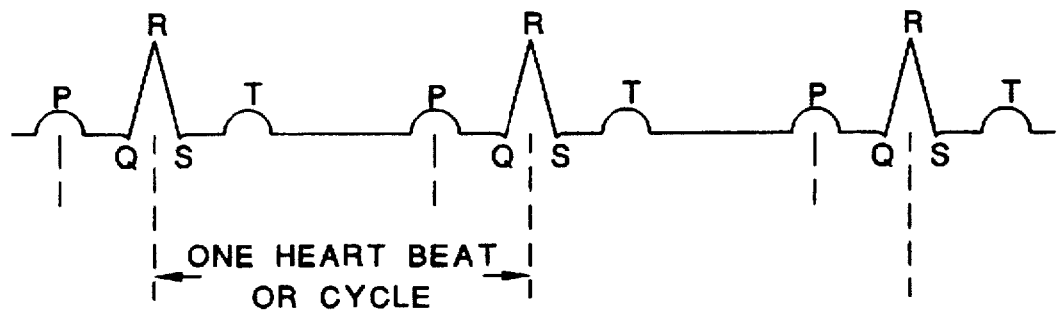

Turning back to FIG. 6A, it is seen that even when the atrial rate is less than the ATDR (NO branch of block 108), and the atrial rate is less than MTR (NO branch of block 109), a determination is made as to whether the atrial rate is within a zone of rates where 2:1 block may occur. To better understand how such a zone of rates is determined, reference is made to the timing diagram of FIGS. 11 and 12. FIG. 11 shows a basic cardiac cycle. The cycle includes a P-wave (evidencing depolarization of the atria) followed by an R-wave (evidencing depolarization of the ventricles). A T-wave is also usually evident (evidencing repolarization of the ventricles). This process repeats during each cardiac cycle, i.e., each cardiac cycle includes depolarization of the atria, followed by depolarization of the ventricles, as explained previously. The cardiac cycle depicted in FIG. 11 is a natural, or non-paced, cardiac cycle.

When a pacemaker is employed, then the pacemaker steps in, as needed, to provide an atrial stimulus (A-pulse) and/or ventricular stimulus (V-pulse) in order to cause appropriate atrial and/or ventricular depolarization at the proper time within the cardiac cycle so as to maintain a desired cardiac rhythm. It does this, as is known in the art, see, e.g., U.S. Pat. No. 4,712,555, by generating several different timed intervals that begin upon the occurrence of certain sensed events. At least three of these timed intervals are important to the present invention. These are the PV delay (or PV interval), the absolute refractory period that follows a V-pulse, and the maximum tracking rate (MTR). Other timing intervals used by the pacemaker during which P-waves are not tracked, such as the post ventricular atrial refractory period (PVARP) may also be important. The PV delay and the absolute refractory period are illustrated in the timing diagrams of FIG. 12A, 12B and 12C.

Figure 12A:
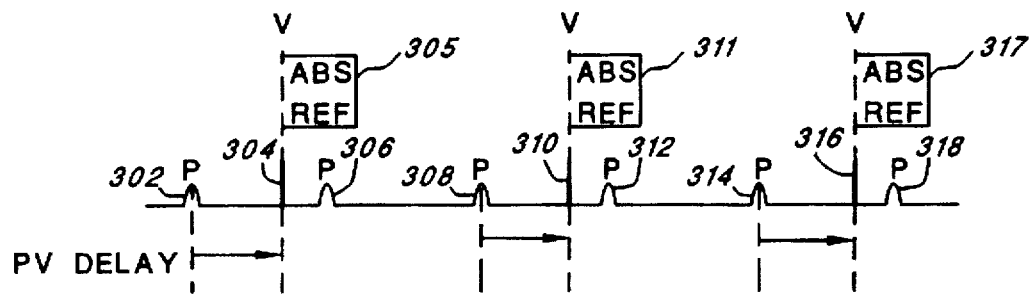
Figure 12B:
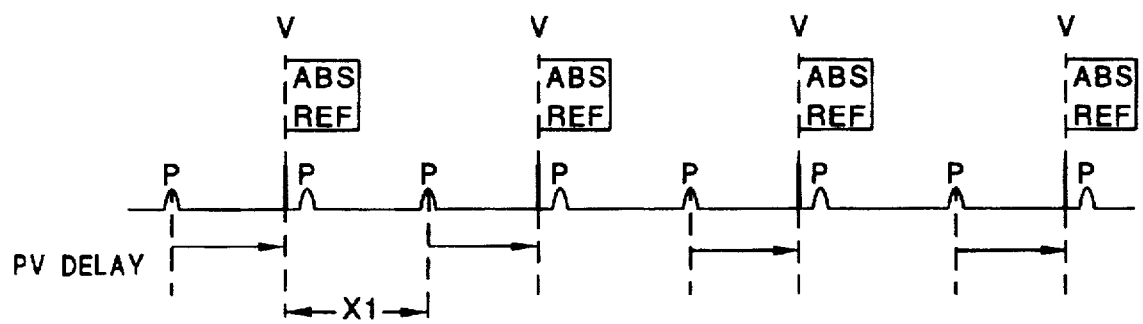
Figure 12C:
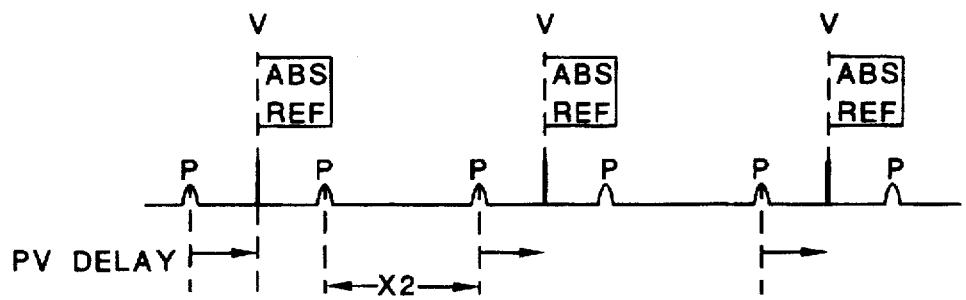

In the timing diagram of FIG. 12A, a cardiac rhythm is depicted wherein a V-pulse 304 is generated one PV delay after a P-wave 302 is sensed. As a result of the V-pulse 304 being generated in the ventricular channel, or as a result of atrial activity in the atrial channel, an absolute refractory time period 305 is present in the atrial channel that follows the V-pulse 304. During such absolute refractory time period, P-waves cannot be sensed. (Note, for purposes of the present discussion, the origin of the absolute refractory time period 305 is not significant. Rather, it is the existence of the absolute refractory time period in the atrial channel following the V-pulse that is significant.) Subsequently, another P-wave 308 is sensed, and another V-pulse 310 is generated one PV delay thereafter. Likewise, yet another P-wave 314 is sensed, with yet an additional V-pulse being generated one PV delay thereafter. This process continues, with the absolute refractory period 305 following the V-pulse 304, an absolute refractory period 311 following the V-pulse 310, and an absolute refractory period 317 following the V-pulse 316.

For the condition illustrated in FIG. 12A, additional P-waves 306, 312 and 318 are also present. But the P-waves 306, 312 and 318 occur at a time during the cardiac cycle coinciding with the absolute refractory periods 305, 311 and 317, respectively. Hence, these P-waves 306, 312 and 318 are "hidden" P-waves, and are not detected by the pacemaker circuitry. (P-waves could also be hidden within any other non-P-wave-tracking interval that may be used by the pacemaker, such as a PVARP interval.) Thus, the atrial rate determined by the pacemaker for the condition illustrated in FIG. 12A would be determined by the interval between P-wave 302 and P-wave 308, or between P-wave 308 and P-wave 314, which atrial rate would only be about ½ of the true atrial rate because every other P-wave remains hidden. Such a condition is known as "2:1 block" because every other P-wave is blocked from being tracked. Because the blocking occurs within the absolute refractory period, the P-wave also will not be detected or sensed even if the pacer looks at sensed activity within PVARP and/or the PV interval to determine atrial rate. For purposes of the present application, this type of 2:1 block (wherein neither tracking nor sensing can occur) is referred to as 2:1 sensing block. (It is also possible for most P-waves of a given P-wave sequence to be sensed, but wherein an occasional third, fourth or fifth P-wave slips into whatever non-P-wave-tracking interval may be present, and therefore to become hidden.)

A 2:1 sensing block condition as shown in the timing diagram of FIG. 12A only occurs within a certain atrial rate zone. Because P-waves may be hidden within this rate zone, the atrial rate must often be assumed based on the measured ventricular rate. The rate zone during which 2:1 sensing block occurs is that range of rates wherein the PV delay plus the absolute refractory period (or other non-P-wave-sensing interval) following the V-pulse combine to define a total sensing block period (a time interval wherein P-waves are not sensed) that blocks regularly-occurring P-waves from being sensed. At an upper end of such a 2:1 rate zone, illustrated in the timing waveform diagram of FIG. 12B, a hidden P-wave occurs very early in the absolute refractory (or other non-P-wave sensing) period, i.e., immediately after, or coincident with, the generation of a V-pulse. At a lower end of the 2:1 rate zone, depicted in the timing waveform diagram of FIG. 12C, a hidden P-wave occurs very near or at the end of the absolute refractory (or other non-P-wave sensing) period. The upper rate at which hidden P-waves may occur is thus bounded by an upper ventricular pacing rate limit (in bpm) equal to the lesser of: (1) ½×60,000/PVI, where PVI is the PV interval (in msec), 60,000 is a beats-per-millisecond to beats-per-minute conversion factor, and ½ is a conversion factor used to account for the fact that only every other P-wave is followed with a ventricular stimulus; or (2) MTR, where MTR is the maximum tracking rate of the pacemaker (in bpm). The lower rate at which hidden P-waves may occur is similarly bounded by a lower ventricular pacing rate limit (in bpm) of ½×60,000/(PVI+ARP), where ARP is the absolute refractory period (in msec) that follows the V-pulse. Note, when a 2:1 sensing block condition is present, the observed atrial rate is ½ of the true atrial rate; or, said differently, the observed P-to-P interval is twice as long as the true P-to-P interval. The true P-to-P interval at the upper rate limit is shown as X1 in FIG. 12B, where X1 approaches the limit PVI; and as X2 in FIG. 12C, where X2 approaches the limit PVI+ARP.

By way of example, if the PVI is set to 150 msec and the ARP is set to 100 msec, and the MTR of the pacemaker is set at 150 bpm, then a 2:1 sensing block condition can occur when the observed atrial rate is between about 120 to 150 bpm, i.e., when the ventricular pacing rate is also between about 120 to 150 bpm. Hence, with reference to the flow diagram of FIG. 6A, at block 110, if the observed atrial rate, or the ventricular pacing rate, is between about 120 and 150 bpm when the above pacemaker settings are used, then a determination is made (YES branch of block 110) that the atrial rate is within a 2:1 sensing block zone. If so, then a further optional determination may be made as to whether the observed atrial rate is stable (block 112), e.g., whether the variations in the observed P-to-P interval over a prescribed number of cardiac cycles, such as 3 to 5 cardiac cycles, are such that all detected P-waves are within the 2:1 sensing block range. If yes, then a determination is made as to whether it is time to sample the AIEGM for hidden P-waves (block 114). Typically, a sampling rate of n cardiac cycles, where n is a programmable integer of between 4 and 128 is initially set.

If it is time to sample for hidden P-waves (YES branch of block 114), then the AIEGM is examined for hidden P-waves (block 120). Several different procedures may be invoked to uncover hidden P-waves in accordance with the present invention, as detailed more fully below in conjunction with FIGS. 7-10. Should a hidden P-wave be uncovered (block 130), then the actual or true atrial rate is determined based on the uncovered P-wave and other sensed P-waves (block 140). In some instances, preference may be given to the uncovered P-waves in determining the atrial rate, although typically both uncovered P-waves and regularly sensed P-waves will be used in determining the atrial rate. If the true atrial rate determined in this manner is greater than the atrial tachycardia detection rate, ATDR (block 150), then the operating mode of the pacer is automatically switched to a non-atrial synchronous mode (block 152, FIG. 6B). If the true atrial rate is less than the ATDR, or if any of the prior determinations (blocks 110, 112, 114, 130) are negative, then pacing continues in the atrial synchronous mode (block 104).

As described above, it is thus seen that the present invention provides a pacemaker wherein an automatic mode switch occurs from an atrial synchronous mode to a non-atrial synchronous mode in the event that the true atrial rate, determined in part from uncovering hidden P-waves, is greater than an ATDR.

Referring to FIG. 6B, it is seen that the invention further provides for more than just a mode switch in the event the true atrial rate is greater than the ATDR. The invention may also invoke an antitachycardia pacing (ATP) feature. If such ATP feature is programmed ON (block 154), and if the atrial rate is stable (block 156), then such ATP feature is also invoked (block 158). The type of ATP that is carried out may be any of the ATP features known in the art, see, e.g., U.S. Pat. No. 5,103,822, or yet to be developed. Typically, ATP features involve some type of burst pacing, followed up with one or more back-up V-pulses, but the actual type of ATP feature that is carried out is not important to the present invention. Rather, what is important is that whatever ATP feature is available, and programmed ON, be invoked.

Even after ATP is invoked, following a mode switch, additional therapy may be called upon to break the atrial tachycardia. For example, if atrial shock defibrillation therapy is available within the implantable medical device, and if any ATP therapy that was previously invoked was unsuccessful, and if such shock-therapy is programmed ON (block 160), then such atrial defibrillation shock therapy may also be invoked (block 162).

After the atrial defibrillation shock therapy has been invoked (block 162), or after a determination has been made that such therapy is either not available or not programmed ON (NO branch of block 160), then the non-atrial synchronous mode pacing is performed (block 164). While such non-atrial synchronous mode pacing is being carried out, the atrial rate is periodically or regularly checked (block 166). If a determination is made that the atrial rate is less than a preset or preprogrammed maximal tracking rate (MTR), then the pacemaker automatically switches back to the atrial synchronous mode (block 168), and atrial synchronous mode pacing is carried out as described above (blocks 104 through 150). A typical MTR for an implantable pacemaker may be 100 to 175 bpm.

As described above, it is thus seen that the present invention also provides for the application of available ATP features with ventricular backup, and/or atrial defibrillation shock therapy, in addition to a mode switch to a non-atrial synchronous mode of pacing, in an attempt to break an atrial tachycardia, once the presence of such atrial tachycardia has been detected based on the uncovering of hidden P-waves.

Turning next to FIGS. 7-10, and related timing diagrams of FIGS. 13-17, various techniques are disclosed that are used by a pacemaker operating in accordance with the present invention to uncover hidden P-waves. This uncovering of hidden P-waves when the pacer is operating below MTR is depicted in FIG. 6A as blocks 120 and 130. The input to block 120 is a connector block "A" 170. The two possible outputs from block 130 (YES, P-wave uncovered; or NO, P-wave not uncovered) pass through connector blocks "B" and "C", labeled with reference numerals 172 and 174, respectively. These connector blocks 170, 172 and 174 are included in FIGS. 7-10 to depict how the processes shown in these figures merge within the overall flow diagram of FIG. 6A.

Figure 13:
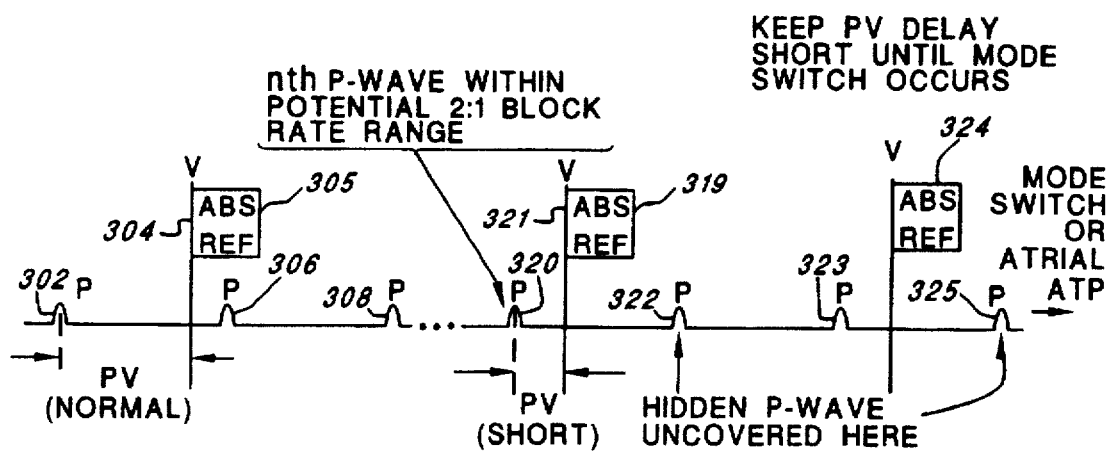
Figure 14:
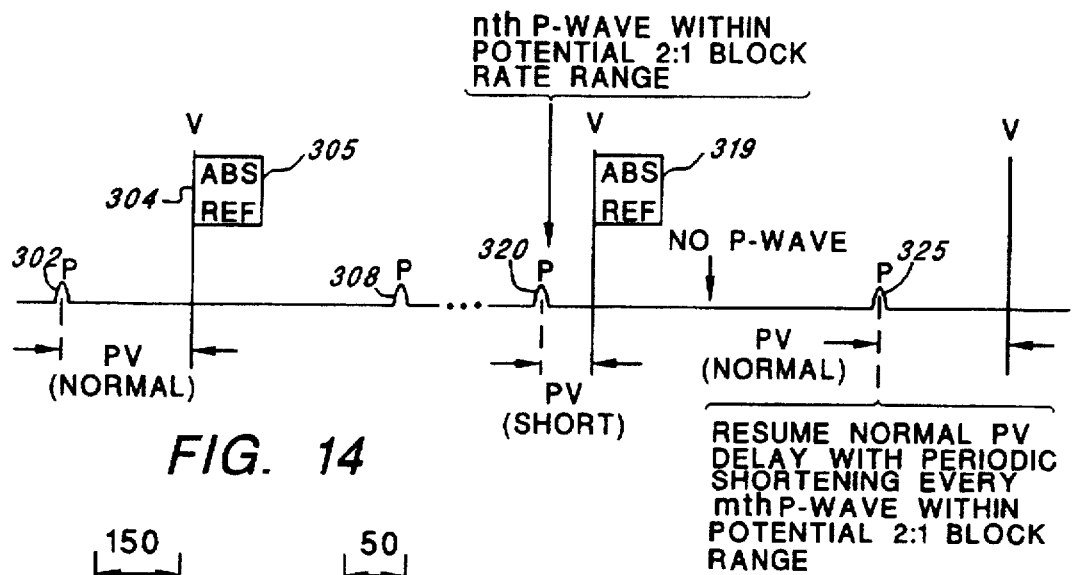

The basic process of shortening the PV delay to uncover a hidden P-wave is best understood with reference to the timing waveform diagrams of FIGS. 13 and 14. In FIG. 13, it is assumed that every other P-wave, e.g., P-wave 306, is hidden by the absolute refractory period following the V-pulse. Hence, after n P-waves have occurred within a potential 2:1 sensing block rate range, the PV delay is shortened. Thus, in FIG. 13, after the P-wave 320, which represents the nth P-wave to have occurred within a potential 2:1 sensing block rate range, the PV delay following the P-wave 320 is shortened. This shortening of the PV delay causes the V-pulse 321 that follows the PV delay to occur at a different time within the cardiac cycle. Hence, the absolute refractory period 319 that follows the V-pulse 321 is time shifted within the cardiac cycle, thereby uncovering any hidden P-waves, i.e., the P-wave 322, that may have been hidden behind the absolute refractory period 319 prior to its time shift. Once a hidden P-wave is uncovered in this manner, the PV delay is kept short until the appropriate mode switch and/or other ATP therapy takes place.

Should a hidden P-wave not be uncovered after the PV delay is shortened following the nth P-wave that occurs within a potential 2:1 sensing block rate range, as depicted in FIG. 14, then the normal PV delay is resumed following the next P-wave 325. Thereafter, even though the P-waves may continue to occur at a potential 2:1 sensing block rate range, the PV delay is only periodically shortened, e.g., every m cardiac cycles, to determine if any hidden P-waves are present. Representative values for n and m are 10 and 512, respectively.

It is also possible to lengthen the PV delay, rather than shorten it, after n cardiac cycles have occurred at a P-wave rate that is within a potential 2:1 sensing block rate range. Such lengthening would achieve the same basic over-all effect of time-shifting the absolute refractory period within the cardiac cycle so as to uncover any hidden P-waves that may exist. Lengthening the PV delay, however, at least for some patients, will enhance retrograde conduction. Hence, although the present invention may uncover hidden P-waves by either shortening or lengthening the PV delay, the preferred technique is to shorten the PV delay.

As described, it is seen that the present invention thus samples for hidden P-waves fairly soon, e.g., after 10 cardiac cycles, after determining that the rate of P-waves lies within a potential 2:1 sensing block rate range; but once having sampled for hidden P-waves and not finding any, the sampling rate for hidden P-waves is thereafter significantly reduced, e.g., looking for hidden P-waves only after 512 cardiac cycles have occurred. This shifting of the sampling rate advantageously allows hidden P-waves to be uncovered fairly rapidly when the conditions are right for such hidden P-waves to occur; but also allows the normal tracking of P-waves to continue with minimum interruption or sampling when hidden P-waves are not initially uncovered.

Figure 15A:
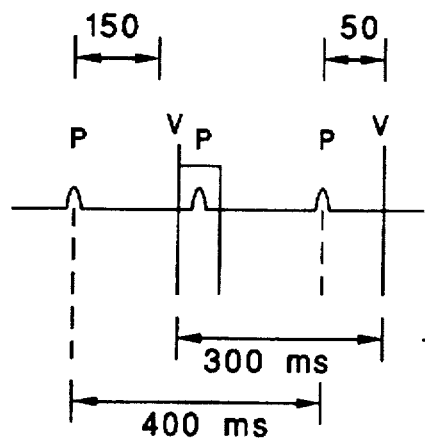
Figure 15B:
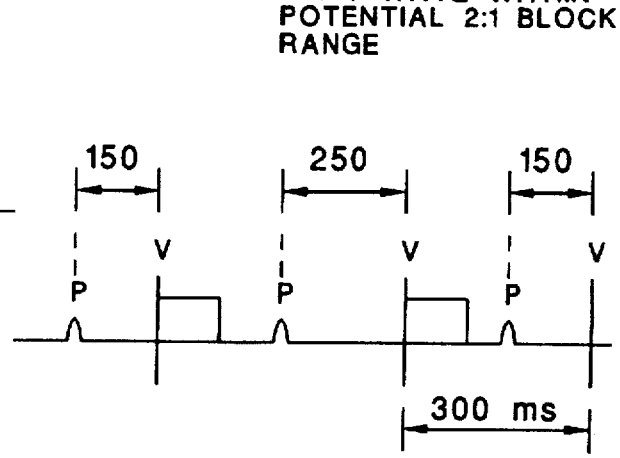

A potential problem may be created when the PV delay is shortened (or lengthened) as described above in that the V-to-V interval may be shortened to values that create an excessively high ventricular rate, at least momentarily, for the patient. This potential problem is illustrated in the timing waveform diagrams of FIGS. 15A and 15B. In FIG. 15-1, a measured P-to-P rate of 400 msec exists, and a hidden P-wave is present. If the PV delay were to be shortened from 150 msec to 50 msec, then the next V-to-V interval would be shortened to 300 msec, a value that corresponds to a ventricular rate of 1/300 msec, or approximately 200 bpm. Such ventricular rate, when produced by V-pulses, may be much too fast for most patients. Similarly, in FIG. 15-2, if the PV delay were to be lengthened from 150 msec to 250 msec, and thereafter returned to 150 msec, a V-to-V interval of 300 msec could result.

In order to avoid V-to-V intervals that may be too short, as shown in FIGS. 15A and 15B, the present invention preferably utilizes a decremental shortening of the PV delay as depicted in the timing waveform diagram of FIG. 16. In FIG. 16, it is assumed that the measured P-to-P interval represents an atrial rate within a potential 2:1 sensing block rate range, and that n P-waves have occurred at this rate. Hence, in accordance with the invention, the PV delay is shortened in an attempt to uncover any hidden P-waves that may be present. However, rather than shorten the PV delay in one step, the PV delay may be decrementally shortened by a set amount each cycle, e.g., 25 msec. Alternatively, the PV delay may be shortened each cycle by an amount calculated to provide a V-to-V interval that is greater than or equal to the maximum tracking rate interval (MTRI) minus a set amount, e.g., 25 msec. Such shortening of the PV interval continues until either a desired minimum PV delay is reached, or until the maximum P-to-P rate that can be measured is greater than a rate of predicted hidden P-waves.

Figure 7:
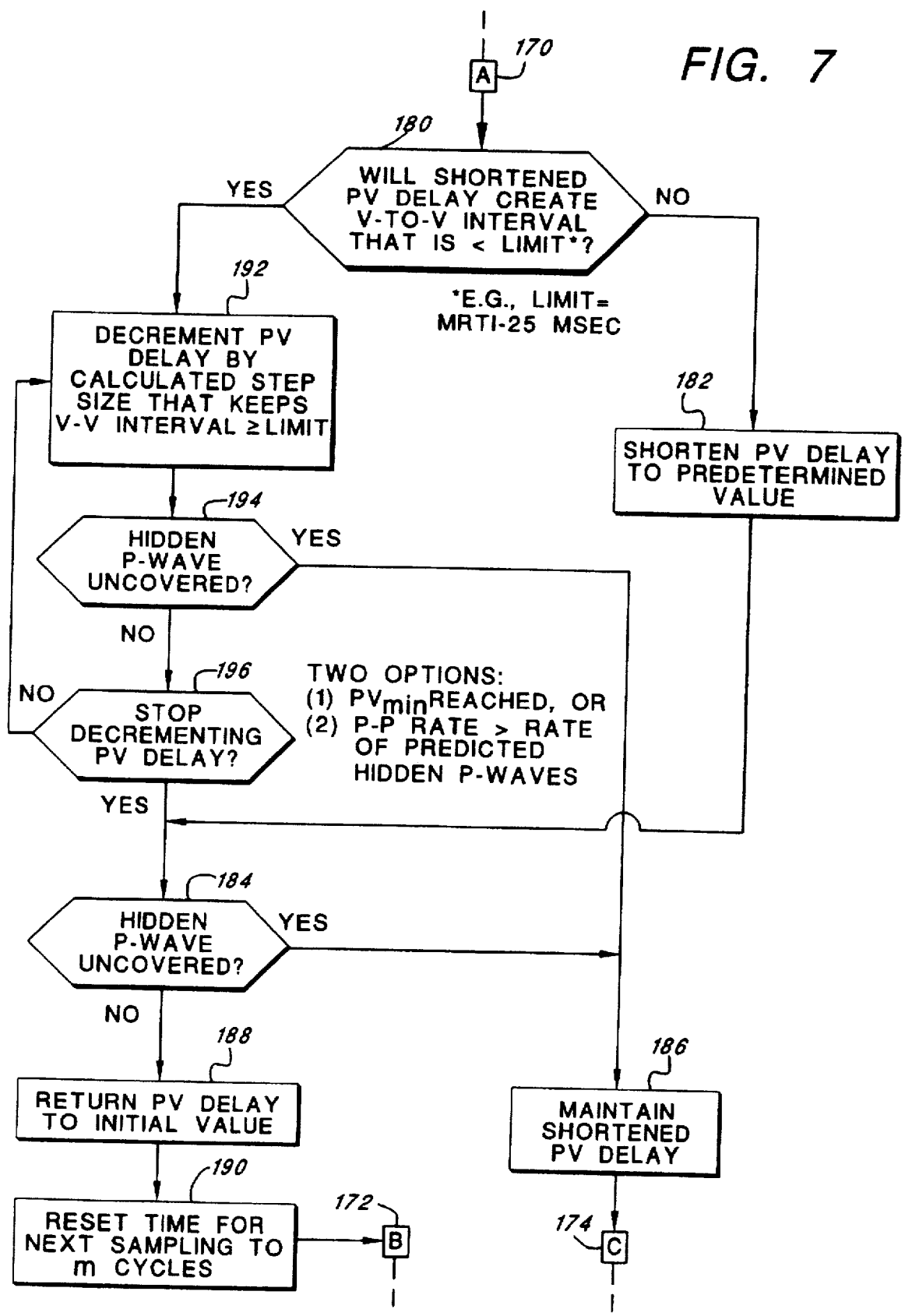
FIG. 7 is a flow chart that depicts one way hidden P-waves are uncovered by decreasing or shortening the PV delay, and wherein the decrementing of the PV delay may be carried out in small steps in order to prevent V-to-V intervals that are too short.
Figure 8:
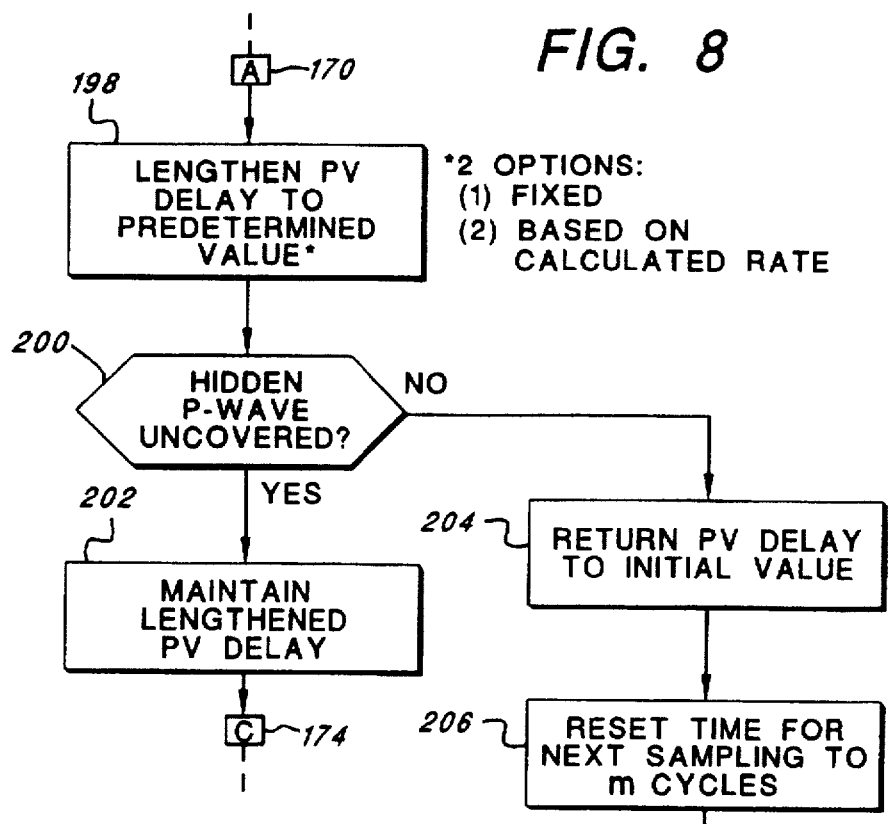
FIG. 8 is a flow chart that depicts an alternative way by which hidden P-waves are uncovered by lengthening the PV delay.

With the foregoing principles of PV shortening and/or lengthening in mind, reference is next made to FIGS. 7 and 8 where there is shown a flow chart of the PV shortening method (FIG. 7) and the PV lengthening method (FIG. 8) utilized by a pacemaker in accordance with the present invention. Referring first to FIG. 7, it is seen that as the hidden P-wave uncovering method begins, at the connection block 170, a decision is initially made as to whether the shortened PV delay will create a V-to-V interval that is less than a preset limit (block 180). The preset limit may be any preselected limit aimed at preventing V-to-V intervals that are too short. For example, the limit may be the MTR interval less 25 msec. If the shortening of the PV interval does not result in a V-to-V interval that is too short (NO branch of block 180), then the PV delay is shortened to the predetermined value (block 182). Once thus shortened, a determination is made as to whether a P-wave is sensed. If so, such P-wave represents an uncovered hidden P-wave (YES branch of block 184). When such a hidden P-wave is uncovered, the PV delay remains short (block 186) until a mode switch and/or other ATP therapy takes place (through connector block 174 to the flow charts of FIGS. 6A and 6B). If a P-wave is not sensed after the PV delay has been shortened, then it is assumed that no hidden P-wave exits (NO branch of block 184), and the PV delay is returned to its prior (non-shortened) value (block 188). Then, the sample time for looking for the next hidden P-wave is reset to m cycles, and the method returns (through connector block 172) to the main flow chart of FIG. 6A and 6B.

If a determination is initially made that a shortened PV delay will create a V-to-V interval that is less than a preset limit (YES branch of block 180), then the PV delay is decremented in a step size that keeps the V-to-V interval to a value greater than or equal to the preset limit, which limit may be, e.g., the MTR interval less 25 msec. As the decrementing is performed, i.e., for each decremented value of the PV delay that is used, a determination may be made as to whether a hidden P-wave is uncovered (block 194). If so, then the PV delay is maintained at its current shortened value (block 186), and the process continues as described previously. Alternatively, the decrementing of the PV delay may continue until no further decrementing is to take place (block 196), and then a determination is made as to whether a hidden P-wave has been uncovered (block 184). Thus, as seen in FIG. 7, hidden P-waves may be sought as the decrementing takes place (as indicated in the optional block 194), or hidden P-waves may be sought after the decrementing has been completed (block 184).

The PV delay is preferably decremented, as described above in connection with block 196, until one of two PV decrementing termination conditions is reached. A first PV decrementing termination condition is a static condition, and comprises a set minimum value below which the PV delay may not go. In accordance with such static condition, the PV delay is thus decrementally reduced until a minimum value of the PV delay, $PV_{MIN}$, is reached. The value of $PV_{MIN}$ is typically in the range of 50 msec. Thus, e.g., if the PV delay is initially 150 msec, and if the measured P-to-P interval is equal to the MTRI, and $PV_{MIN}$ is 50 msec, four decrementing steps may be used, providing a respective PV delay of 125 msec, 100 msec, 75 msec, and then 50 msec, to reach $PV_{MIN}$.

A second PV decrementing termination condition is a dynamic condition, and comprises reducing the PV delay until the maximum P-to-P rate that can be measured is greater than the rate of predicted hidden P-waves. Said a different way, the PV delay is reduced using an appropriate step size that assures the V-to-V interval is not reduced below a preset limit. For example, if the PVI is 150 msec, the ARP is 100 msec, and the measured P-to-P interval prior to the uncovering procedure is 461 msec ($\approx$130 bpm), then shortening the PVI to some value just less than 130 msec (461 msec/2–100 msec) may uncover an atrial rate twice as fast as the measured atrial rate.

FIG. 8 depicts the PV lengthening approach that may be used by the invention. Once the method commences, at connection block 170, the PV delay is lengthened to a predetermined value (block 198). Such predetermined value may be a fixed value, or may be a calculated value (e.g., based on the measured atrial rate prior to lengthening). After lengthening the PV delay, a determination is made as to whether a hidden P-wave is uncovered (block 200). If so, the lengthened PV delay is maintained until an appropriate mode switch and/or other ATP therapy takes place (see FIG. 6A and 6B, through connector block 174). If no hidden P-wave is uncovered, then the PV delay is returned to its initial value (block 204), and the time for the next sampling for hidden P-waves is set to m cycles (block 206). Then, atrial synchronous pacing continues (through block 172 to block 104 of FIG. 6A). Note, in block 204, where the PVI is returned to its initial value, that the PVI will be decremented so as to maintain the V-to-V interval greater than or equal to a predefined limit (e.g., the MTRI–25 msec).

Figure 9:
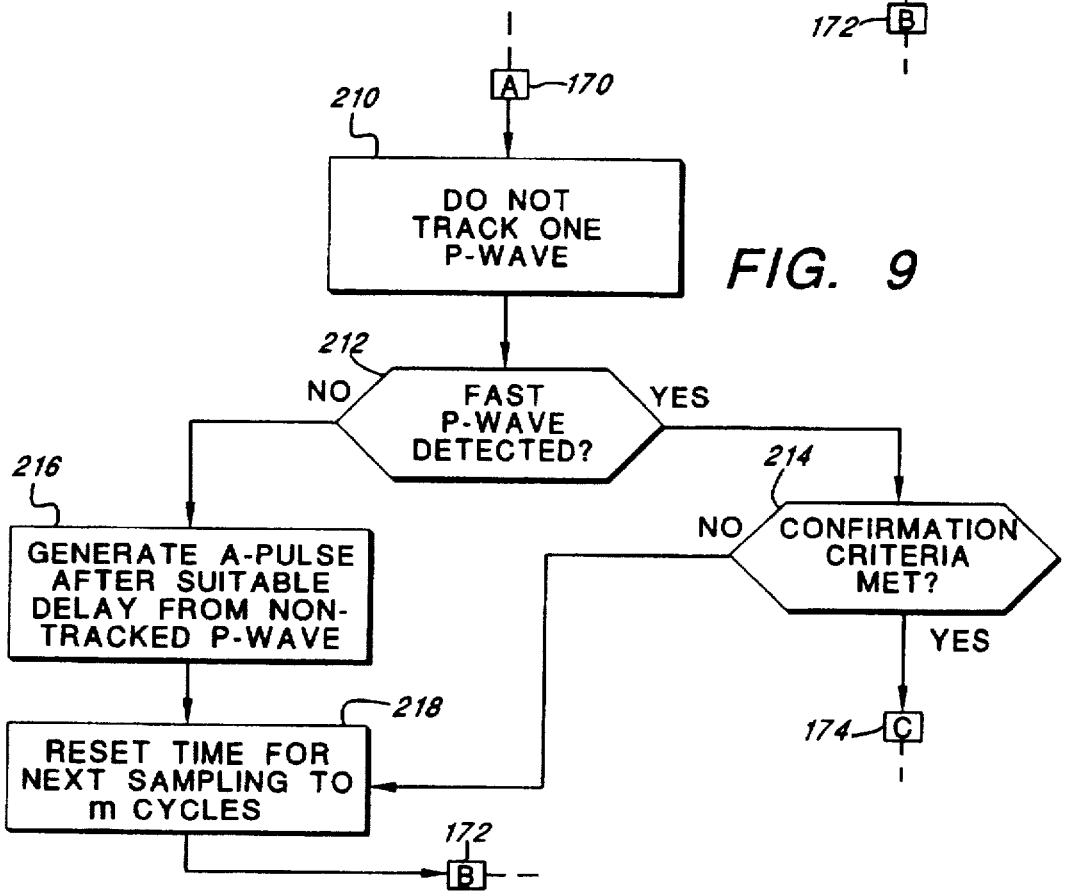
FIG. 9 is a flow chart that depicts yet another way by which hidden P-waves are uncovered by periodically not tracking a P-wave.

Turning next to FIGS. 9 and 17, a different technique for uncovering a hidden P-wave is depicted. This technique does not involve time shifting the absolute refractory period (or other non-P-wave-tracking periods) within the cardiac cycle, but rather involves not tracking the nth sensed P-wave. When a P-wave is not tracked, that means no V-pulse is generated after the non-tracked P-wave. Hence, no absolute refractory (or other) period is generated that could hide or mask out a P-wave. As a result, any P-wave which would have remained hidden by the absolute refractory (or other) period is uncovered, and the presence or absence of such hidden P-wave following the non-tracked P-wave may be readily determined. (As indicated previously, a P-wave that is uncovered using this selective non-tracking technique is sometimes referred to as a "fast P-wave" because it appears sooner in the cardiac sequence than do non-hidden P-waves.)

Referring then to FIG. 9, it is seen that this method or technique involves, as a first step, not tracking a P-wave (block 210). Typically, the P-waves sensed in the AIEGM are simply counted, and when the nth P-wave at a rate greater than the 2:1 sensing block rate lower limit is encountered, it is not tracked. After not tracking the nth P-wave, a determination is made as to whether a fast P-wave is detected (block 212). If so (YES branch of block 212), and if certain prescribed confirmation criteria are present (block 214), then such fast P-wave is deemed to represent a fast atrial rate, and the process continues as described above in FIGS. 6A and 6B at connector block 174. The confirmation criteria may require, for example, that fast P-waves be detected in this manner for 3 to 8 consecutive non-tracked cardiac cycles, with a P-to-P rate greater than the ATDR, or as otherwise described below.

If a fast P-wave is not encountered (NO branch of block 212), then an A-pulse is generated after a suitable delay (e.g., 350 msec) from the non-tracked P-wave (block 216), and the reset time for the next sampling for hidden P-waves is set to m cycles (block 218). Likewise, in the event a fast P-wave is detected, but the confirmation criteria is not met (NO branch of block 214), the reset time is also set to m cycles (block 218). After resetting the sampling time, the process continues based on not finding a hidden P-wave as described above in FIGS. 6A and 6B at connector block 172.

Still with reference to the method described in FIG. 9, and also with reference to the timing waveform diagram of FIG. 17, it is seen that should a fast P-wave not be detected (NO branch of block 212 in FIG. 9), then an A-pulse is generated after a suitable delay from the non-tracked P-wave (block 216 in FIG. 9). This generation of an A-pulse is further illustrated as "Case 2" in FIG. 17. As seen in FIG. 17, Case 2, the nth P-wave, identified by the reference numeral 328, is not tracked. Following the nth P-wave, no fast P-wave is detected. As a result, after a suitable delay from the non-tracked nth P-wave, e.g., 350 msec., an A-pulse 330 is generated. This A-pulse 330 is generated so that a V-pulse 332 can follow soon thereafter, e.g., one AV delay thereafter (where this AV delay is the same as, or shorter than, the programmed AV delay). In this manner, even though the P-wave 328 is not tracked, thereby disrupting momentarily the cardiac rhythm, the A-pulse 330 is quickly generated, thereby reinstating an appropriate cardiac rhythm for the pacemaker patient.

Should the non-tracking of the nth P-wave 328 reveal a fast P-wave 332, as depicted in Case 1 and Case 3 in FIG. 17 (and as indicated in the YES branch of block 212 in FIG. 9), then a determination is made as to whether an appropriate confirmation criteria is present (block 214 of FIG. 9), i.e., whether the fast P-wave actually represents the recurrence of hidden P-waves, or whether it simply represents a one-time anomaly.

At least two different confirmation criteria may be applied. In FIG. 17, Case 1, after the fast P-wave 332 is uncovered, a determination is made as to the fast P-to-P interval (PPI) time between the non-tracked P-wave 328 and the uncovered fast P-wave 332. Then, the P-to-P interval is monitored for the next x cycles. If this P-to-P interval remains at roughly two times the fast PPI, then that provides a good indication that the fast P-wave 332 truly represented a hidden P-wave. The value of x may be from 2 to 20 cycles. In such case, a mode switch is made after the confirmation criteria has been confirmed, i.e., after the x cardiac cycles.

In FIG. 17, Case 3, after the fast P-wave 332 is uncovered, the fast P-wave is tracked so that a V-pulse 334 is generated one PV delay thereafter. Further, the fast PPI is determined between the non-tracked P-wave 328 and the fast P-wave 332. The next sensed P-wave 336 is again not tracked, and a determination made as to whether not tracking the P-wave 336 results in the detection of yet another fast P-wave 338. If so, the PPI is again determined, and the fast P-wave 338 is tracked, resulting in another V-pulse. Again, the next sensed P-wave 342 is not tracked. If yet another fast P-wave 344 is detected following the third non-tracked P-wave 342, then the PPI is again determined. If fast P-waves are detected for at least, e.g., three consecutive times, and if the PPI determined for such fast P-waves indicates an actual atrial rate that exceeds the atrial tachycardia detection rate (ATDR), then the confirmation criteria for the fast P-waves has been determined, and a mode switch may take place, as indicated in blocks 140 and 150 in FIGS. 6-1 and 6-2.

Figure 10:
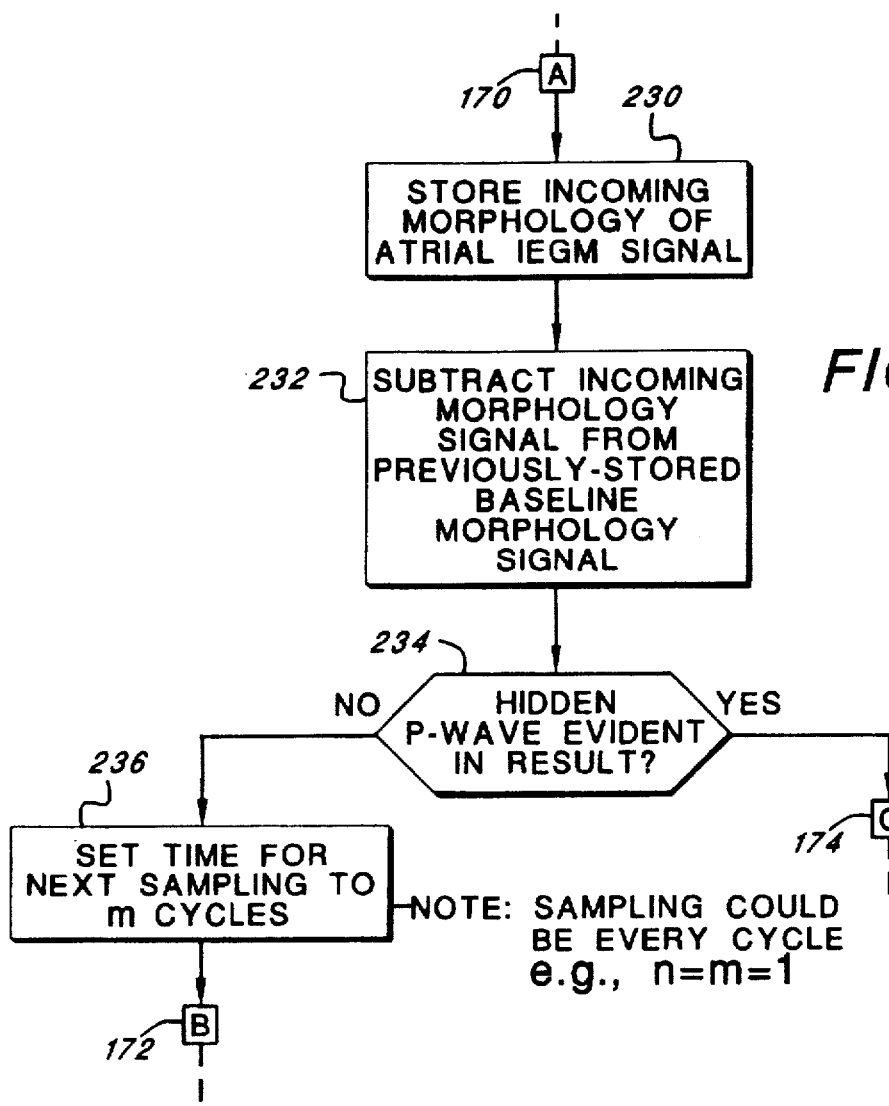
FIG. 10 illustrates still an alternative method for uncovering hidden P-waves by comparing the morphology of the incoming AIEGM to a previously-stored baseline AIEGM morphology.

Turning next to FIG. 10, a flow chart is shown that illustrates yet an additional technique that may be used to determine the presence of a hidden P-wave. The technique shown in FIG. 10 compares the morphology (shape) of the incoming AIEGM signal (the "AIEGM" signal is the atrial intracardiac electrogram signal) during the time when the absolute refractory period would normally be present (i.e., following a V-pulse) to a previously-stored baseline morphology of the same signal in order to determine if a P-wave is present. The technique described in connection with FIG. 10 is conceptually illustrated in FIG. 20, which depicts the exposure of a hidden P-wave by subtracting out a far-field R-wave baseline waveform.

As seen in FIG. 10, as soon as it is time to look for hidden P-waves, which begins at input block 170, the morphology of the AIEGM signal is stored (block 230) for a select window of time during the cardiac cycle. This stored morphology is then subtracted from a previously-stored baseline morphology of the same signal, but taken at a time when no hidden P-waves were present (block 234). If a hidden P-wave is present within the incoming AIEGM signal, then the result of such subtraction will reveal its presence. Hence, if a P-wave is evident from the subtraction (YES branch of block 234), then a hidden P-wave is deemed present, and the overall process continues as described above in connection with FIGS. 6A and 6B at block 174. If a P-wave is not evident from the subtraction (NO branch of block 234), then it is assumed that no hidden P-waves are present, and the sample time for again looking for another hidden P-wave is set to m cycles (block 236). Then, the process continues as described above in connection with FIGS. 6A and 6B at block 172. It is noted that in the case shown in FIG. 10, where the morphology of the incoming signal is compared with a baseline morphology, sampling could occur as frequently as every cycle, e.g., n=m=1.

The morphology of the incoming AIEGM signal, as well as the baseline morphology of the AIEGM signal, may be obtained in conventional manner. See, e.g., U.S. Pat. No. 4,552,154, or U.S. patent application Ser. No. 07/984,157, filed Dec. 1, 1992 now abandoned, entitled "Cardiac Event Detection in Implantable Medical Devices", which application is assigned to the same assignee as the present application. Both the '154 patent and above patent application are incorporated herein by reference.

Typically, the morphology of the AIEGM signal is measured by sampling the AIEGM signal at a fairly rapid rate, e.g., every 0.5 to 2 milliseconds, digitizing the sampled signal at each sample time, and storing the digitized sample for each sample time in a suitable memory storage element. There may thus be a series of memory addresses where the baseline morphology signal is stored as a function of the IEGM sample time. Then, as the incoming AIEGM signal is sampled and digitized, each digitized sample is subtracted from the corresponding digitized baseline sample for the same sample time. In theory, in the absence of a hidden P-wave, the basic morphology of the incoming AIEGM signal should not change. Hence, the difference between the morphology of the present incoming AIEGM signal and the baseline AIEGM signal should be zero. In practice, however, there will be some changes due to sampling errors, etc. Thus, as the digitized sample of the incoming AIEGM signal is subtracted from the corresponding digitized sample of the baseline morphology, the result may be compared to a preset or preprogrammed threshold value, and/or stored. If a sufficient number of such results exceed the threshold, then that may be used as an indication that a hidden P-wave is present. Alternatively, the actual morphology of the difference signal can be plotted and/or examined to determine if it reflects the anticipated shape and/or timing of a hidden P-wave.

The baseline morphology signal, in accordance with the method shown in FIG. 10, may be stored automatically on a periodic basis, or as otherwise controlled by an attending physician or medical personnel. Preferably, the baseline morphology is taken when the atrial rate is relatively slow, thereby minimizing the likelihood that a hidden P-wave may be present. Also, the baseline morphology preferably reflects an average of the morphology of several baseline cardiac cycles, e.g., 3 to 8 cardiac cycles.

It is noted that throughout the description of the invention presented above, frequent reference has been made to the PV interval, or PV delay. For purposes of this patent application, the PV interval or PV delay should be considered as the time interval between atrial channel activity, whether such atrial channel activity comprises an A-pulse or a P-wave, and the subsequent delivery of a ventricular stimulation pulse (V-pulse).

While the invention herein disclosed has been described by means of specific embodiments and applications thereof, numerous modifications and variations could be made thereto by those skilled in the art without departing from the scope of the invention set forth in the claims.

What is claimed is:

1. A method of determining the atrial rate of a patient in a dual-chamber implantable pacemaker, the pacemaker including: sensing means for sensing P-waves; pulse generation means for generating V-pulses; timing means for defining a PV delay that defines a time interval allowed by the pacemaker between a sensed P-wave and a generated V-pulse, a basic pacing interval that defines a pacing rate, and an absolute refractory period following generation of a V-pulse during which P-waves are not sensed; the method comprising:

(a) sensing a series of consecutive P-waves to determine an atrial rate;

(b) determining if the atrial rate is within an atrial rate zone where P-waves may be hidden within the absolute refractory period;

(c) if hidden P-waves may exist, examining that portion of the basic pacing interval corresponding to the absolute refractory period to determine if a hidden P-wave lies therewithin; and (d) if a hidden P-wave is uncovered within the absolute refractory period, including such hidden P-wave within the series of consecutive P-waves sensed in step (a) to redetermine the atrial rate; whereby the atrial rate is determined based on the inclusion of such hidden P-wave.

2. The method of claim 1, wherein step (c) comprises time-shifting the refractory period within the basic pacing interval.

3. The method of claim 2, wherein time-shifting the refractory period comprises shortening the PV delay.

4. The method of claim 3, further comprising incrementally shortening the PV delay in increments that prevent a V-to-V interval of the pacemaker from becoming less than a prescribed limit.

5. The method of claim 4, wherein the prescribed limit to which the V-to-V interval is limited is a maximum track rate (MTR) interval less k milliseconds.

6. The method of claim 5, wherein k comprises 10 to 50 milliseconds.

7. The method of claim 4, wherein the PV delay is incrementally shortened until a minimum PV delay is reached.

8. The method of claim 4, wherein the PV delay is incrementally shortened until a P-to-P interval is measured corresponding to a P-to-P rate that is faster than a predicted rate of hidden P-waves.

9. The method of claim 3, wherein time-shifting the refractory period comprises lengthening the PV delay.

10. The method of claim 1, wherein step (c) comprises ceasing to track a sensed P-wave, which sensed P-wave becomes a non-tracked P-wave, and not generating a V-pulse following the non-tracked P-wave, whereby no absolute refractory period is generated, the absolute refractory period thereby being removed from the basic pacing interval, thereby uncovering any P-waves that occur during the time period of the basic pacing interval as the absolute refractory period would have occurred had a V-pulse been generated.

11. The method of claim 10, further including generating an A-pulse y milliseconds after the non-tracked P-wave if no hidden P-wave is uncovered following the non-tracked P-wave, where y is a predetermined value.

12. The method of claim 11, where the value of y is at least 300 milliseconds and less than 500 milliseconds.

13. The method of claim 10, further including:
measuring the interval between the non-tracked P-wave and an uncovered P-wave, if present, as a fast P-to-P interval;
measuring the interval between two of the series of consecutive P-waves sensed in step (a) as a sensed P-to-P interval;
comparing the sensed P-to-P interval to the fast P-to-P interval to see if the sensed P-to-P interval is about twice as long as the fast P-to-P interval; and if so,
determining the atrial rate based on the fast P-to-P interval.

14. The method of claim 13, further including switching an operating mode of the pacemaker from an atrial synchronous mode to a non-atrial synchronous mode if the atrial rate is faster than a preset atrial tachycardia detection rate (ATDR).

15. The method of claim 14, further including confirming the atrial rate, and if confirmed, performing atrial tachycardia pacing (ATP) in accordance with a predefined pacing pattern.

16. The method of claim 10 wherein, if a first P-wave is uncovered, the following additional steps are included:
measuring the interval between the non-tracked P-wave and the uncovered first P-wave as a first fast P-to-P interval,
tracking the uncovered first P-wave by generating a V-pulse one PV delay thereafter;
not tracking the next sensed P-wave so as to uncover a second P-wave, p1 measuring the interval between the most recent non-tracked P-wave and the uncovered second P-wave as a second fast P-to-P interval, and
determining the atrial rate based on at least the first and second fast P-to-P intervals.

17. The method of claim 16, further comprising:
tracking an nth uncovered P-wave by generating a V-pulse one PV delay thereafter, where n is an integer greater than one;
not tracking the next sensed P-wave so as to uncover an (n+1)th P-wave;
measuring the interval between the nth non-tracked P-wave and the uncovered (n+1)th P-wave as an (n+1)th fast P-to-P interval; and
further determining the atrial rate based on the (n+1)th fast P-to-P interval.

18. The method of claim 1, wherein the implantable pacemaker includes means for operating in either an atrial synchronous mode or a non-atrial synchronous mode, and wherein the method further includes:
(e) determining if the atrial rate exceeds a preset atrial tachycardia detection rate (ATDR), and if so, automatically switching the mode of operation of the pacemaker from an atrial synchronous mode to a non-atrial synchronous mode.

19. The method of claim 1, wherein the implantable pacemaker includes means for applying an antitachycardia pacing (ATP) procedure to break an atrial tachycardia, and wherein the method further includes:
(e) determining if the atrial rate exceeds a preset atrial tachycardia detection rate (ATDR), and if so, automatically invoking the ATP procedure.

20. The method of claim 1, wherein the implantable pacemaker also includes means for performing atrial defibrillation shock therapy, and wherein the method further comprises:
(e) determining if the atrial rate exceeds a preset atrial tachycardia detection rate (ATDR), and if so, applying the atrial defibrillation shock therapy.

21. The method of claim 1, wherein step (b) is carried out on a sampled basis.

22. The method of claim 21, wherein step (b) is initially carried out every n cardiac cycles.

23. The method of claim 21, further including sampling for hidden P-waves every m cardiac cycles in the event a hidden P-wave is not uncovered, where m is much greater than n.

24. The method of claim 23, wherein n is at least 8, and m is at least 100.

25. The method of claim 1, wherein the pacemaker further includes means for applying an antitachycardia pacing (ATP) therapy, and wherein the method further includes analyzing the atrial rate determined in step (d) to ascertain whether the atrial rate indicates the need to apply ATP therapy, and if so, applying such ATP therapy.

26. The method of claim 1, further including giving preference to any uncovered P-waves as the atrial rate is determined in step (d).

27. The method of claim 1, wherein step (c) comprises storing a baseline morphology of an intracardiac electrogram (IEGM) signal for that portion of the basic pacing interval corresponding to the absolute refractory period, and thereafter measuring a morphology of the IEGM signal to obtain a measured morphology, and comparing the measured morphology to the baseline morphology to determine if a hidden P-wave is present within the measured morphology.

28. The method of claim 27, wherein the step of comparing the measured morphology to the baseline morphology comprises subtracting the baseline morphology from the measured morphology.

29. The method of claim 1, wherein step (c) further includes sensing if atrial activity is present and uncovering a hidden P-wave only when sensed atrial activity is present in order to confirm that the uncovered hidden P-wave is a true P-wave and not a far-field R-wave.

30. A method of uncovering hidden P-waves that occur during the absolute refractory period following a ventricular stimulus of a dual-chamber implantable pacemaker, the pacemaker including: sensing means for sensing P-waves; pulse generation means for generating V-pulses; timing means for defining a PV delay that defines a time interval allowed by the pacemaker between a sensed P-wave and a generated V-pulse, a basic pacing interval that defines a pacing rate, and an absolute refractory period following generation of a V-pulse during which P-wave sensing is not reliable; the method comprising:

moving the absolute refractory period away from that portion of the basic pacing interval wherein hidden P-waves may lie; and sensing whether any P-waves occur within that portion of the cardiac cycle from which the absolute refractory period has been moved, and if so, identifying such sensed P-waves as hidden P-waves.

31. The method of claim 30, wherein the step of moving the absolute refractory period comprises time shifting the absolute refractory period within the cardiac cycle by changing the duration of the PV delay.

32. The method of claim 31, wherein the step of changing the duration of the PV delay comprises shortening the PV delay.

33. The method of claim 32, wherein the step of shortening the duration of the PV delay comprises incrementally shortening the PV delay over several cardiac cycles so as to maintain a minimum V-to-V interval.

34. The method of claim 31, wherein the step of changing the duration of the PV delay comprises lengthening the PV delay.

35. The method of claim 30, wherein the step of moving the absolute refractory period comprises:

counting and tracking P-waves for n−1 cardiac cycles, where n is a prescribed number;

not tracking a P-wave during the nth cardiac cycle, whereby no PV delay is generated in the nth cardiac cycle, and no V-pulse is generated in the nth cardiac cycle, thereby moving the absolute refractory period from the nth cardiac cycle.

36. A method of determining the atrial rate of a patient having a dual-chamber pacemaker, the pacemaker including: sensing means for sensing P-waves; pulse generation means for generating V-pulses; timing means for defining a basic pacing interval that defines a pacing rate and a maximum tracking rate (MTR) interval (MTRI) that limits the rate at which V-pulses are generated; the method comprising:

determining if V-pulses are generated at a rate that is limited by the MTR, and if so sensing P-waves that occur during the MTRI and classifying such P-waves as non-tracked P-waves, sensing P-waves that occur outside the MTRI and classifying such P-waves as tracked P-waves, and determining the atrial rate as a function of a P-to-P interval separating the consecutive sensed P-waves, whether such consecutive P-waves are non-tracked or tracked;

whereby the consecutive sensed P-waves define the determined atrial rate.

37. The method, as set forth in claim 36, wherein the pacemaker further includes non-tracked time intervals during which P-waves are not tracked, and wherein the method further comprises using P-waves sensed during such non-tracked time intervals to help determine the atrial rate.

38. A method for determining the presence of an atrial tachycardia in a patient having a dual-chamber pacemaker, the pacemaker comprising:

means for defining an atrial tachycardia detection rate (ATDR);

sensing means for sensing P-waves;

pulse generation means for generating a ventricular stimulation pulse (V-pulse) a prescribed time delay following a sensed P-wave; and timing means for defining and generating a fixed, recurring, free-running atrial lock interval (ALI*) that is independent from any sensed cardiac events, the ALI* thus comprising a sequence of recurring fixed periods of length ALI*, the method comprising:

determining in more than one V-pulse would be generated in any given ALI* period, and if so, inhibiting all but the first V-pulse in any given ALI* period, measuring a P-to-P interval (PPI) for each inhibited V-pulse as the time interval between a first sensed P-wave following which the inhibited V-pulse would have been generated and a second sensed P-wave immediately following the first sensed P-wave, determining if the PPI for i consecutive inhibited V-pulses corresponds to an atrial rate greater than the ATDR, where i is an integer greater than one, and if so declaring an atrial tachycardia condition to be present.

39. The method, as set forth in claim 38, wherein the integer i comprises at least three.

40. A dual-chamber implantable pacemaker that detects atrial rate based on sensed P-waves, including sensed P-waves that are potentially hidden within an absolute refractory period, comprising:

sensing means for sensing a series of consecutive P-waves;

pulse generation means for generating V-pulses;

timing means for defining a PV delay that defines a time interval allowed by the pacemaker between a sensed P-wave and a generated V-pulse, a basic pacing interval that defines a pacing rate, and an absolute refractory period following generation of a V-pulse during which P-waves are not sensed;

control means for examining that portion of the basic pacing interval corresponding to the absolute refractory period to uncover any hidden P-waves that lie therewithin; and rate-determining means for determining a true atrial rate based on all sensed P-waves, including any uncovered hidden P-waves.

41. The implantable pacemaker, as set forth in claim 40, wherein the control means comprises means for controlling the timing means so that the duration of the PV delay is systematically varied to time shift the occurrence of the absolute refractory period within a given pacing cycle.

42. The implantable pacemaker, as set forth in claim 40, wherein the control means comprises means for controlling the timing means so that the PV delay is not generated for certain P-waves, whereby such certain P-waves are not tracked, and no V-pulse is generated a PV delay thereafter.

43. A mode-switching pacemaker that automatically switches modes based on an atrial rate sensed by the pacemaker comprising:

sensing means for sensing a series of consecutive P-waves;

pulse generation means for generating V-pulses;

timing means for defining a PV delay that defines a time interval allowed by the pacemaker between a sensed P-wave and a generated V-pulse, a basic pacing interval that defines a pacing rate, and an absolute refractory period following generation of a V-pulse during which P-waves are not sensed;

control means for operating the pacemaker in an atrial synchronous mode and for examining that portion of the basic pacing interval corresponding to the absolute refractory period to uncover any hidden P-waves that lie therewithin;

rate-determining means for determining a true atrial rate based on all sensed P-waves, including any uncovered hidden P-waves; and mode switching means for switching the mode of the pacemaker to a non-atrial synchronous mode in the event the atrial rate determined by the rate-determining means exceeds a preset atrial tachycardia detection rate (ATDR).

44. The mode switching pacemaker, as set forth in claim 43, wherein the rate-determining means comprises means for determining a true atrial rate based primarily on non-tracked sensed P-waves, a non-tracked sensed P-wave comprising a P-wave that is not followed by the PV delay.

* * * * *